United States Patent
Holmes

(10) Patent No.: US 12,070,437 B2
(45) Date of Patent: Aug. 27, 2024

(54) AUTOMATIC PACKAGER FOR PHARMACEUTICALS AND METHOD OF OPERATING THE SAME

(71) Applicant: RXSAFE LLC, Vista, CA (US)

(72) Inventor: William K. Holmes, San Diego, CA (US)

(73) Assignee: RXSAFE LLC, Vista, CA (US)

( * ) Notice: Subject to any disclaimer, the term of this patent is extended or adjusted under 35 U.S.C. 154(b) by 814 days.

(21) Appl. No.: 17/045,217

(22) PCT Filed: Apr. 4, 2019

(86) PCT No.: PCT/US2019/025905
§ 371 (c)(1),
(2) Date: Oct. 5, 2020

(87) PCT Pub. No.: WO2019/195629
PCT Pub. Date: Oct. 10, 2019

(65) Prior Publication Data
US 2021/0161767 A1    Jun. 3, 2021

Related U.S. Application Data

(60) Provisional application No. 62/652,692, filed on Apr. 4, 2018, provisional application No. 62/745,126, filed on Oct. 12, 2018.

(51) Int. Cl.
*A61J 7/00* (2006.01)
*A61J 7/02* (2006.01)
(Continued)

(52) U.S. Cl.
CPC .......... *A61J 7/0076* (2013.01); *A61J 7/0069* (2013.01); *A61J 7/02* (2013.01); *B65B 9/02* (2013.01);
(Continued)

(58) Field of Classification Search
CPC .. A61J 7/02; A61J 7/0076; B65B 9/02; B65B 35/12; B65B 57/145
See application file for complete search history.

(56) References Cited

U.S. PATENT DOCUMENTS 5,522,512 A * 6/1996 Archer ...................... B07C 5/38
                                                    209/580
5,564,593 A * 10/1996 East, Sr. ............... A61J 7/0481
                                                    221/121
(Continued)

FOREIGN PATENT DOCUMENTS

CA    2620159 C    12/2014
CA    2790220 C    6/2016
(Continued)

OTHER PUBLICATIONS

Third Office Action issued from the Chinese Patent Office for related Application No. 201980023827.5 dated Nov. 9, 2022 (8 pages including English Translation).
(Continued)

*Primary Examiner* — Lucas E. A. Palmer
(74) *Attorney, Agent, or Firm* — Michael Best & Friedrich LLP

(57) ABSTRACT

Automatic packager for pharmaceuticals and method of operating the same. The method includes receiving a prescription to be filled by a pharmacy management system and identifying one or more bulk containers that contain medications to fill the prescription. The method also includes counting, using a pre-counter, medications from the one or more bulk containers to fill the prescription and depositing the counted medications in one or more cartridges. The method also includes placing the one or more cartridges including the counted medications at an automatic packager and dispensing the medications in the one or more cartridges. The method also includes packaging medications
(Continued)

dispensed from the one or more cartridges into packages and verifying whether the medications are correctly packaged.

27 Claims, 17 Drawing Sheets

(51) Int. Cl.
  *B65B 9/02*     (2006.01)
  *B65B 35/12*    (2006.01)
  *B65B 57/14*    (2006.01)
  *G16H 20/13*    (2018.01)
  *G16H 40/20*    (2018.01)
  *G16H 70/40*    (2018.01)
(52) U.S. Cl.
  CPC ............ *B65B 35/12* (2013.01); *B65B 57/145* (2013.01); *G16H 20/13* (2018.01); *G16H 40/20* (2018.01); *G16H 70/40* (2018.01)

(56) References Cited

U.S. PATENT DOCUMENTS

| | | | | |
|---|---|---|---|---|
| 5,765,606 | A * | 6/1998 | Takemasa | G07F 17/0092 141/234 |
| 6,006,946 | A * | 12/1999 | Williams | G07F 17/0092 221/9 |
| 6,219,587 | B1 * | 4/2001 | Ahlin | G07F 17/0092 700/233 |
| 6,611,733 | B1 * | 8/2003 | De La Huerga | G06K 19/07762 700/235 |
| 6,761,010 | B1 * | 7/2004 | Gibson | A61J 7/0084 53/247 |
| 6,799,685 | B1 * | 10/2004 | Yuyama | G07F 17/0092 209/552 |
| 6,892,512 | B2 * | 5/2005 | Rice | B65B 5/103 53/445 |
| 7,599,516 | B2 | 10/2009 | Limer et al. | |
| 8,467,897 | B2 | 6/2013 | Holmes et al. | |
| 8,511,478 | B2 * | 8/2013 | Terzini | B65B 43/50 209/621 |
| 8,682,047 | B2 | 3/2014 | Lang et al. | |
| 8,861,816 | B2 | 10/2014 | Lang et al. | |
| 8,943,779 | B2 * | 2/2015 | Amano | G06V 20/66 378/57 |
| 9,449,148 | B2 | 9/2016 | Holmes | |
| 9,727,701 | B2 | 8/2017 | Holmes et al. | |
| 9,868,558 | B2 | 1/2018 | Holmes | |
| RE46,910 | E * | 6/2018 | Aylward | B65B 37/08 |
| 10,187,593 | B2 | 1/2019 | Holmes | |
| 10,427,809 | B2 | 10/2019 | Holmes | |
| 10,427,810 | B2 | 10/2019 | Holmes | |
| 10,583,941 | B2 * | 3/2020 | Holmes | B65B 57/14 |
| 10,736,819 | B1 | 8/2020 | Nowosielski et al. | |
| 11,410,764 | B1 * | 8/2022 | Rosomoff | A61J 7/0481 |
| 2002/0179619 | A1 * | 12/2002 | Geltser | A61J 7/02 221/2 |
| 2005/0021173 | A1 * | 1/2005 | Pinney | G07F 11/62 700/231 |
| 2005/0267356 | A1 * | 12/2005 | Ramasubramanian | A61J 1/03 600/411 |
| 2007/0189597 | A1 | 8/2007 | Limer et al. | |
| 2008/0300719 | A1 * | 12/2008 | Duke | G07F 9/026 221/206 |
| 2009/0012820 | A1 * | 1/2009 | Bishop | G06Q 10/087 705/3 |
| 2009/0076841 | A1 * | 3/2009 | Baker | G16H 40/20 705/2 |
| 2010/0074496 | A1 * | 3/2010 | Pao | G06T 7/0012 382/190 |
| 2010/0277888 | A1 | 11/2010 | Yeh | |
| 2011/0146835 | A1 * | 6/2011 | Terzini | G16H 70/40 141/98 |
| 2011/0184751 | A1 | 7/2011 | Holmes | |
| 2011/0303692 | A1 * | 12/2011 | Kim | G07F 11/44 221/124 |
| 2012/0216485 | A1 * | 8/2012 | Amano | G07F 17/0092 53/64 |
| 2012/0239188 | A1 * | 9/2012 | Sugimoto | B65B 61/025 221/133 |
| 2013/0018503 | A1 * | 1/2013 | Carson | B65D 75/327 700/216 |
| 2013/0020345 | A1 * | 1/2013 | Kim | B65B 37/04 221/9 |
| 2013/0218326 | A1 * | 8/2013 | Chudy | G07F 9/026 700/216 |
| 2013/0284755 | A1 * | 10/2013 | Yuyama | B65G 47/1464 221/277 |
| 2015/0154750 | A1 * | 6/2015 | Royaee | B07C 5/3422 382/128 |
| 2015/0190312 | A1 * | 7/2015 | Yuyama | A61J 7/02 700/232 |
| 2016/0023787 | A1 * | 1/2016 | Joplin | B65B 43/46 198/340 |
| 2016/0114925 | A1 * | 4/2016 | Yuyama | G16H 30/20 382/141 |
| 2016/0199260 | A1 * | 7/2016 | Andersen, Sr. | B65B 57/06 53/235 |
| 2017/0312178 | A1 * | 11/2017 | Patel | B65B 7/16 |
| 2017/0355476 | A1 * | 12/2017 | Kim | B65B 57/14 |
| 2017/0357775 | A1 * | 12/2017 | Ekin | A61J 7/0481 |
| 2018/0012439 | A1 | 1/2018 | King et al. | |
| 2018/0060525 | A1 * | 3/2018 | Chen | B65B 37/18 |
| 2018/0125760 | A1 | 5/2018 | Chessa et al. | |
| 2018/0147120 | A1 * | 5/2018 | Poirier | A61J 7/0076 |
| 2018/0170591 | A1 * | 6/2018 | Koike | B65B 35/42 |
| 2018/0263853 | A1 * | 9/2018 | Yang | B65B 57/20 |
| 2018/0333335 | A1 * | 11/2018 | Carson | G07F 17/0092 |
| 2019/0112080 | A1 * | 4/2019 | Holmes | B65B 1/30 |
| 2019/0201292 | A1 * | 7/2019 | Krezanoski | A61J 7/02 |
| 2019/0307647 | A1 * | 10/2019 | Greenspan | G16H 10/60 |
| 2020/0129379 | A1 * | 4/2020 | Fukada | A61J 7/02 |
| 2020/0165014 | A1 * | 5/2020 | Holmes | B65B 57/14 |
| 2021/0052468 | A1 | 2/2021 | Whittier | |
| 2021/0086934 | A1 * | 3/2021 | Burkett, Jr. | B65B 59/04 |
| 2022/0204193 | A1 * | 6/2022 | Holmes | B65B 5/103 |
| 2023/0011165 | A1 * | 1/2023 | St. Pierre | B65B 1/30 |
| 2023/0101967 | A1 * | 3/2023 | Holmes | A61J 7/02 53/415 |

FOREIGN PATENT DOCUMENTS

| | | |
|---|---|---|
| CN | 1769138 A | 5/2006 |
| CN | 101028292 A | 9/2007 |
| CN | 104662579 B | 12/2018 |
| JP | H0295373 A | 4/1990 |
| JP | H07-299121 A | 11/1995 |
| JP | H11-206855 A | 8/1999 |
| JP | 2002-096802 A | 4/2002 |
| JP | 2007-330411 A | 12/2007 |
| JP | H11-114025 A | 12/2014 |
| TW | 200930352 A | 7/2009 |
| TW | 608440 B | 12/2017 |
| WO | 2009038378 A2 | 3/2009 |
| WO | 2013105198 A1 | 7/2013 |
| WO | 2014112221 A1 | 7/2014 |
| WO | 2016194680 A1 | 12/2016 |
| WO | 2017217366 A1 | 12/2017 |
| WO | 2019195629 A1 | 10/2019 |

OTHER PUBLICATIONS

International Search Report and Written Opinion for Application No. PCT/US2019/025905 dated Jul. 9, 2019 (12 pages).
International Preliminary Report on Patentability for Application No. PCT/US2019/025905 dated Oct. 15, 2020 (8 pages).
First Office Action issued from the Chinese Patent Office for related Application No. 201980023827.5 dated Jan. 6, 2022 (27 Pages including English Translation).

(56) References Cited

OTHER PUBLICATIONS

Second Office Action issued from the Chinese Patent Office for related Application No. 201980023827.5 dated Aug. 3, 2022 (26 pages including English Translation).
Japanese Patent Office Action for application 2020-545316, dated Jan. 4, 2023 (14 pages with translation).
Extended Search Report issued from the European Patent office for related Application No. 19782180.4 dated Dec. 20, 2021, (11 Pages).
Korean Patent Office Action for Application No. 10-2020-7027835, dated Nov. 27, 2023 (24 pages with translation).
Japanese Patent Office Action for Application No. 2023-118460, dated May 14, 2024 (17 pages with translation).

\* cited by examiner

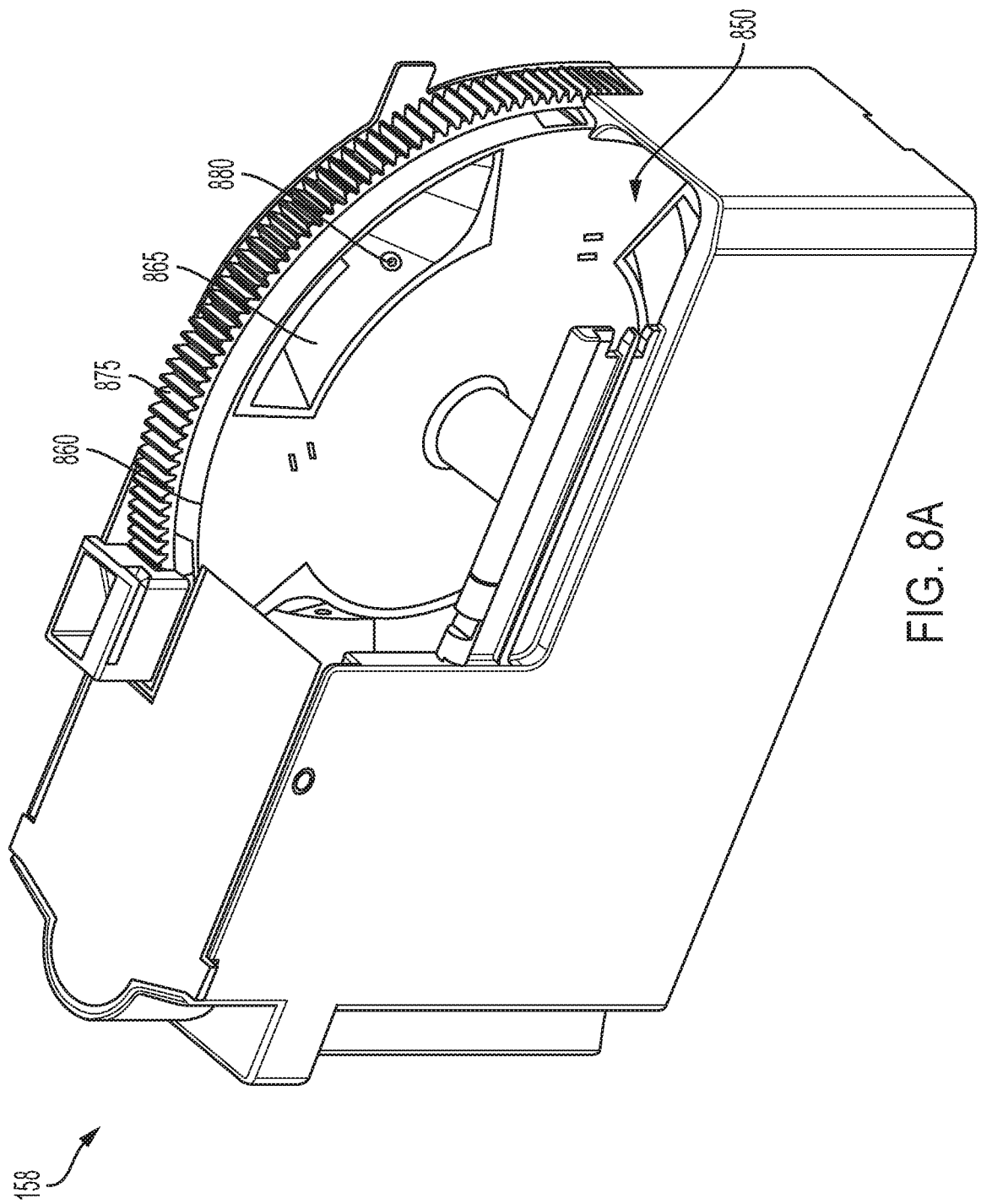

AUTOMATIC PACKAGER FOR PHARMACEUTICALS AND METHOD OF OPERATING THE SAME

CROSS-REFERENCE TO RELATED APPLICATIONS

This application is a national phase filing under 35 U.S.C. 371 of International Application No. PCT/US2019/025905, filed on Apr. 4, 2019, which claims priority to U.S. Provisional Application No. 62/652,692, filed on Apr. 4, 2018, and U.S. Provisional Application No. 62/745,126, filed on Oct. 12, 2018, the entire contents of which are hereby incorporated by reference for all purposes.

FIELD OF THE INVENTION

The present invention relates to pharmaceutical packaging machines and, more particularly, verification systems for packaging machines.

SUMMARY

One embodiment provides a method for filling a prescription in a pharmacy. The method includes receiving, at an electronic processor of a pharmacy management system, a prescription to be filled by the pharmacy management system and identifying, at a pre-counter, one or more bulk containers that contain medications to fill the prescription. The method also includes counting, using the pre-counter, medications from the one or more bulk containers to fill the prescription and depositing the counted medications in one or more cartridges. The method also includes placing the one or more cartridges including the counted medications at an automatic packager and dispensing, using the automatic packager, the medications in the one or more cartridges. The method also includes packaging, using a packaging unit of the automatic packager, medications dispensed from the one or more cartridges into packages and verifying, using the automatic packager, whether the medications are correctly packaged.

Another embodiment provides a method for filling a prescription in a pharmacy. The method includes receiving, at an electronic processor of a pharmacy management system, a prescription to be filled by the pharmacy management system and identifying, at a pre-counter, one or more bulk containers that contain medications to fill the prescription. The method also includes counting, using the pre-counter, medications from the one or more bulk containers to fill the prescription and prompting, using the pre-counter, to add or remove pills from the pre-counter. The method also includes depositing the counted medications in one or more cartridges and placing the one or more cartridges including the counted medications at an automatic packager. The method also includes verifying, using the automatic packager, each medication as the medication is dispensed from the one or more cartridges and packaging, using a packaging unit of the automatic packager, medications dispensed from the one or more cartridges into packages.

Another embodiment provides a method for filling a prescription in a pharmacy. The method includes receiving, at an electronic processor of a pharmacy management system, a prescription to be filled by the pharmacy management system and identifying, at a pre-counter, one or more bulk containers that contain medications to fill the prescription. The method also includes counting, using the pre-counter, medications from the one or more bulk containers to fill the prescription and packaging, using a packaging unit of the automatic packager, medications counted at the pre-counter. The method also includes capturing one or more images of the medications counted at the pre-counter and verifying, using the automatic packager, whether the medications are correctly packaged based on the one or more images of the medications.

Another embodiment provides a method for filling a prescription in a pharmacy. The method includes receiving, at an electronic processor of a pharmacy management system, a prescription to be filled by the pharmacy management system and placing one or more cartridges including medications listed on the prescription at an automatic packager. The method also includes singulating, using the automatic packager, the medications in the one or more cartridges for individually dispensing the medications and verifying, using the automatic packager, each medication while the medication is in the one or more cartridges or as the medication is dispensed from the one or more cartridges. The method also includes capturing an image of the each medication as the medication is dispensed from the one or more cartridges and packaging, using a packaging unit of the automatic packager, medications dispensed from the one or more cartridges into packages. The method also includes verifying, using the automatic packager, whether the medications are correctly packaged.

Another embodiment provides a method for filling a prescription in a pharmacy. The method includes receiving, at an electronic processor of a pharmacy management system, a prescription to be filled by the pharmacy management system and identifying, at a pre-counter, one or more bulk containers that contain medications to fill the prescription. The method also includes counting, using the pre-counter, medications from the one or more bulk containers to fill the prescription and determining, using the pre-counter, one or more characteristics of the medications listed on the prescription. The method also includes transmitting, using the pre-counter, the one or more characteristics of the medications to the automatic packager. The automatic packager verifies the correct medications are packaged by the packaging unit based on the one or more characteristics of the medications received from the pre-counter.

Another embodiment provides a method for filling a prescription in a pharmacy. The method includes receiving, at an electronic processor of a pharmacy management system, a prescription to be filled by the pharmacy management system, and identifying, at a pre-counter, one or more bulk containers that contain medications to fill the prescription. The method also includes counting, using the pre-counter, medications from the one or more bulk containers to fill the prescription, and packaging, using a packaging unit of an automatic packager, medications counted at the pre-counter.

Other aspects of the invention will become apparent by consideration of the detailed description and accompanying drawings.

BRIEF DESCRIPTION OF THE DRAWINGS

FIG. 8A is a perspective view of a cartridge of the automatic packager of FIG. 7 in accordance with some embodiments.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way but may also be configured in ways that are not listed.

Most health treatments require several medications to be administered at particular times during the day. Treatments are not effective if all the required medications are not taken together at the prescribed time. To improve adhesion to a prescription, some pharmacies provide medications in labeled strip packages. Each strip package includes all the different types of medications that should be taken together at the labeled time. Typically, each prescription is provided for medications for the next 30 days. Accordingly, each spool of strip packages includes medications that are provided for the next 30 days.

Each of the strip packages may need to be checked manually to ensure that the correct types and number of medications are included in the strip package. Typically, the strip packages are checked after all of the medications are packaged and removed from the packager. However, if an error was discovered after packaging and labelling, the strip package may need to be removed from the spool and replaced by a correctly packaged and labeled strip package. This provides a break in the spool and is generally inefficient. Additionally, the above method only provides a single opportunity for a pharmacist to identify errors in packaging.

Accordingly, improving the efficiency of verifying the accuracy of packaging and for providing additional opportunities for a pharmacist to efficiently identify or reduce errors in packaging may be desired. Additionally, improving the efficiency in packaging allows the pharmacist to serve additional customers by reducing the amount of time it takes to serve the customers.

Figure 1:
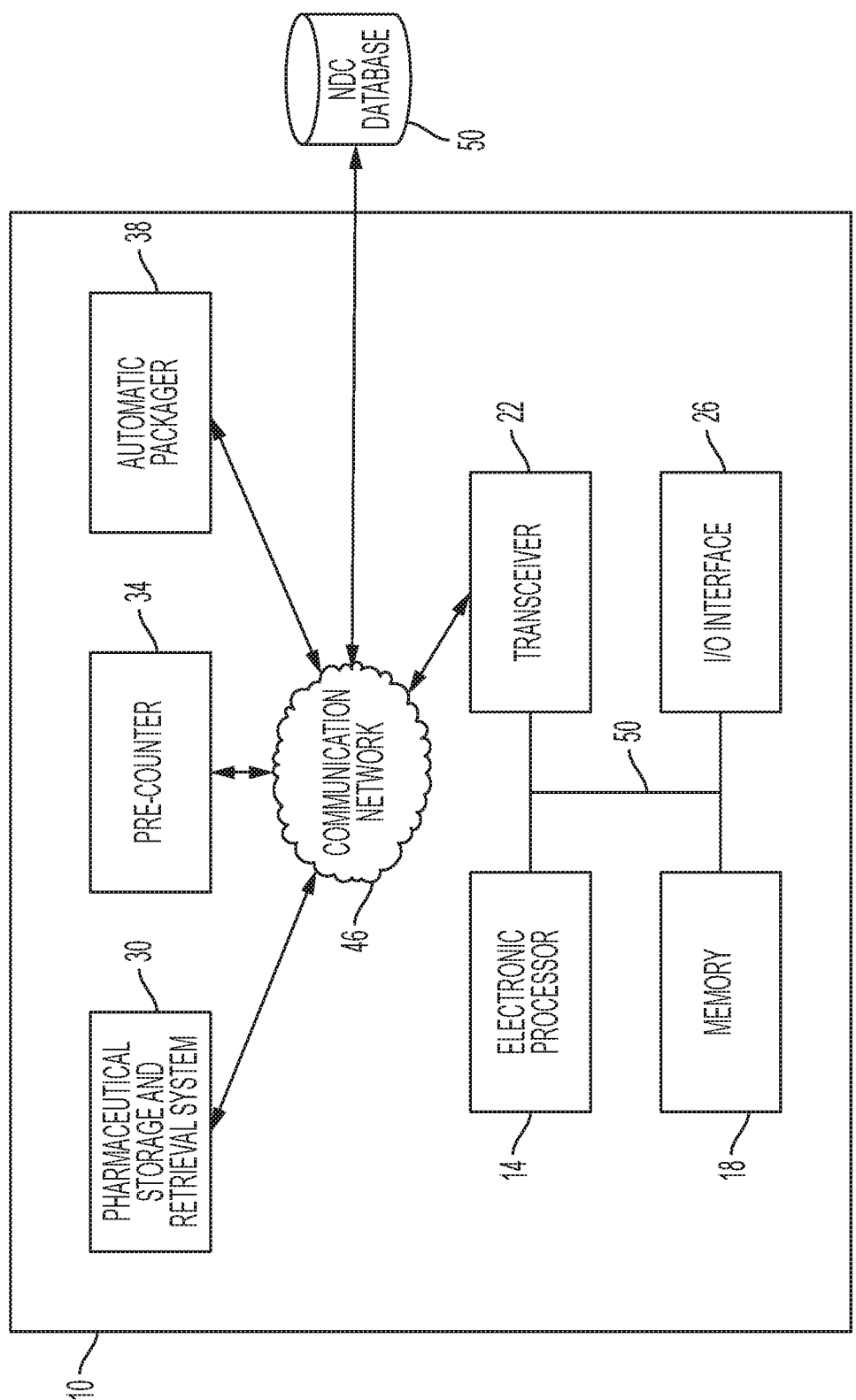
FIG. 1 is a schematic of a pharmacy management system in accordance with some embodiments.

FIG. 1 is a schematic illustration of a pharmacy management system 10 according to one example embodiment. The pharmacy management system 10 is a pharmacy automation system for use in retail pharmacies. The pharmacy management system 10 allows for automation of stocking the pharmacy, filling prescriptions, and inventory control performed in retail pharmacies. In the example illustrated in FIG. 1, the pharmacy management system 10 includes an electronic processor 14, a memory 18, a transceiver 22, an input/output interface 26, a pharmaceutical storage and retrieval system 30, a pre-counter 34, and an automatic packager 38. The electronic processor 14, the memory 18, the transceiver 22, and the input/output interface 26 communicate over one or more control and/or data buses (e.g., a communication bus 42). FIG. 1 illustrates only one exemplary embodiment of the pharmacy management system 10. The pharmacy management system 10 may include more or fewer components and may perform functions other than those explicitly described herein. For example, in some embodiments, the pharmacy management system 10 may not include the pharmaceutical storage and retrieval system 30.

In some embodiments, the electronic processor 14 is implemented as a microprocessor with separate memory, such as the memory 18. In other embodiments, the electronic processor 14 may be implemented as a microcontroller (with memory 18 on the same chip). In other embodiments, the electronic processor 14 may be implemented using multiple processors. In addition, the electronic processor 14 may be implemented partially or entirely as, for example, a field-programmable gate array (FPGA), an application specific integrated circuit (ASIC), and the like, and the memory 18 may not be needed or be modified accordingly. In the example illustrated, the memory 18 includes non-transitory, computer-readable memory that stores instructions that are received and executed by the electronic processor 14 to carry out functionality of the pharmacy management system 10 described herein. The memory 18 may include, for example, a program storage area and a data storage area. The program storage area and the data storage area may include combinations of different types of memory, such as read-only memory and random-access memory.

The transceiver 22 enables wired or wireless communication from the pharmacy management system 10 to a communication network 46. In other embodiments, rather than the transceiver 22, the pharmacy management system 10 may include separate transmitting and receiving components, for example, a transmitter and a receiver. The pharmacy management system 10, through the communication network 46, may communicate with the pharmaceutical storage and retrieval system 30, the pre-counter 34, the automatic packager 38, and databases, for example, the National Drug Code (NDC) database 50.

The communication network 46 can be built according to any suitable networking technology or topology or combinations of technologies and topologies and can include multiple sub-networks. Connections between the devices and systems shown in FIG. 1 can be made through local area networks ("LANs"), wide area networks ("WANs"), public switched telephone networks ("PSTNs"), wireless networks, Intranets, the Internet, or any other suitable networks. In a hospital or medical care facility, for example, communication between the devices and systems shown in FIG. 1 can be made through any required communication protocol(s), including, for example, the Health Level Seven ("HL7") protocol or any other version of a required protocol. The HL7 protocol is a standard protocol which specifies the criteria for data exchange (including the required interface implementation) between two computer applications (sender and receiver), such that a universal standard is used by vendors, thereby facilitating the exchange of electronic data in health care environments. The HL7 protocol allows health care institutions to exchange key sets of data from different application systems. Specifically, the HL7 protocol can define the data to be exchanged, the timing of the interchange, and the communication of errors to the application. The formats are generally generic in nature and can be configured to meet the needs of the applications involved.

Figure 2:
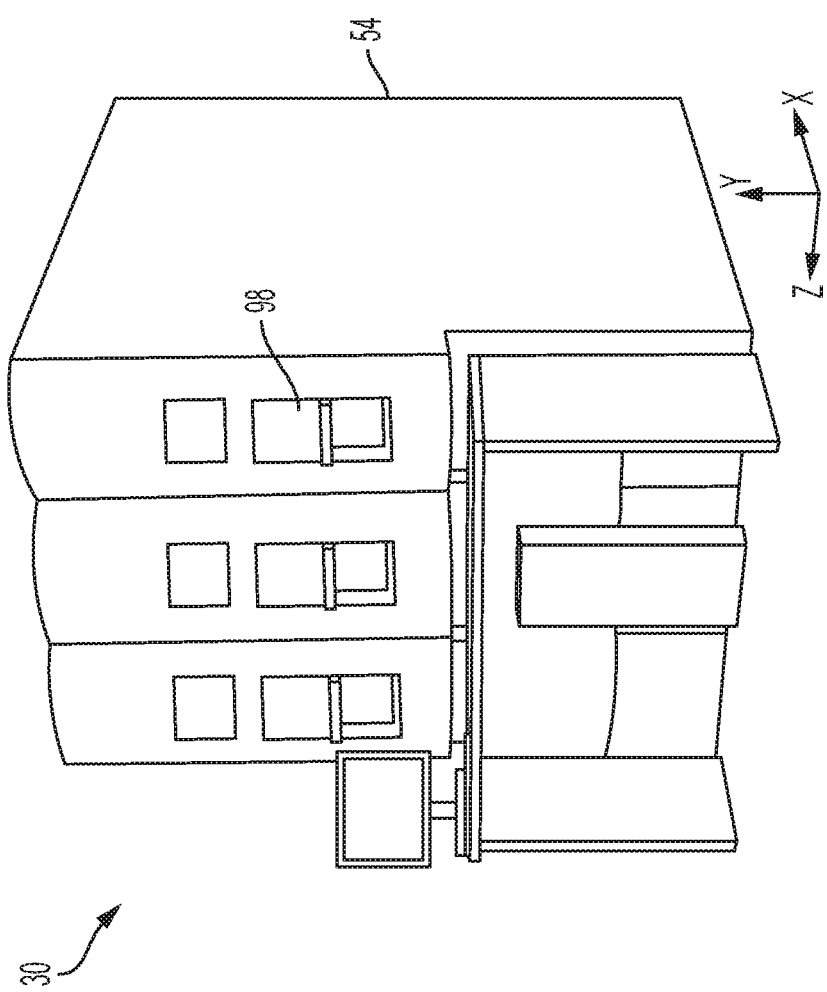
FIG. 2 is a perspective view of a pharmaceutical storage and retrieval system of the pharmacy management system of FIG. 1, the system having three storage and retrieval devices in accordance with some embodiments.

FIG. 2 illustrates a pharmaceutical storage and retrieval system 30 according to one example embodiment. The pharmaceutical storage and retrieval system 30 is a comprehensive workflow automation and high density robotic storage system for use in retail pharmacies. The system 30 seamlessly dispenses prescription containers and returns the containers to inventory without requiring operators to use a complicated software interface. As illustrated in FIG. 1, the pharmaceutical storage and retrieval system 30 includes one or more pharmaceutical storage and retrieval devices 54 and a computer or controller configured to control the operations and functionality of the pharmaceutical storage and retrieval device 54. Although the system 30 shown in FIG. 1 includes three pharmaceutical storage and retrieval devices 54, more or fewer devices 54 can be utilized in a particular pharmaceutical storage and retrieval system 30. Similar pharmaceutical storage and retrieval systems 30 are described and illustrated in U.S. Pat. No. 9,727,701, entitled "PHARMACEUTICAL STORAGE AND RETRIEVAL SYSTEM AND METHODS OF STORING AND RETRIEVING PHARMACEUTICALS," the entire contents of which are hereby incorporated by reference.

Figure 3:
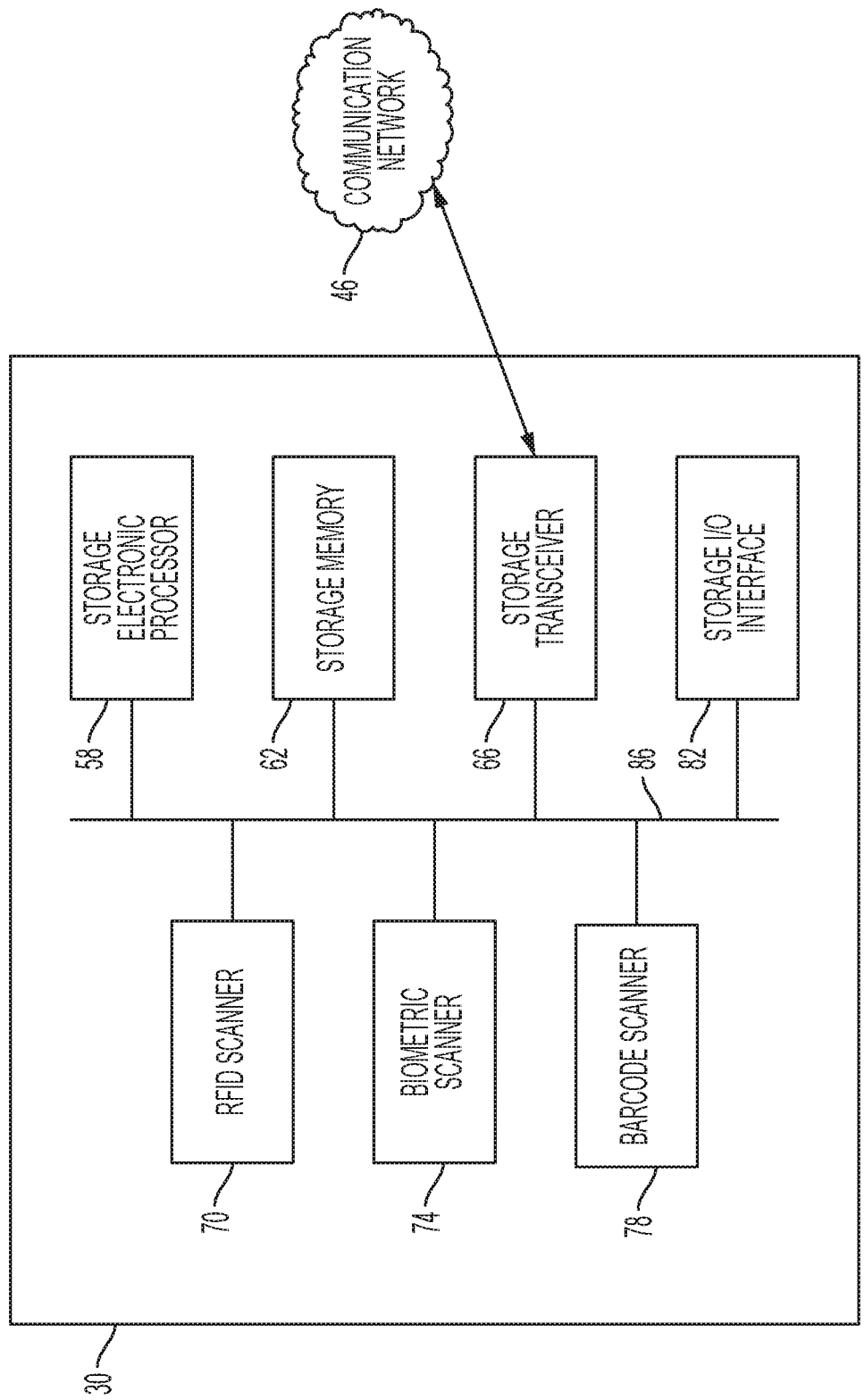
FIG. 3 is a schematic of the pharmaceutical storage and retrieval system illustrated in FIG. 2 in accordance with some embodiments.

FIG. 3 schematically illustrates the pharmaceutical storage and retrieval system 30 and its functionality within a pharmacy. In the example illustrated, the pharmaceutical storage and retrieval system 30 includes a storage electronic processor 58, a storage memory 62, a storage transceiver 66, an RFID scanner 70, a biometric scanner 74, a barcode scanner 78, and a storage input/output interface 82. The storage electronic processor 58, the storage memory 62, the storage transceiver 66, the RFID scanner 70, the biometric scanner 74, the barcode scanner 78, and the storage input/output interface 82 communicate over one or more control and/or data buses (e.g., a communication bus 86). FIG. 3 illustrates only one exemplary embodiment of the pharmaceutical storage and retrieval system 30. The pharmaceutical storage and retrieval system 30 may include more or fewer components and may perform functions other than those explicitly described herein.

The storage electronic processor 58 and the storage memory 62 may be implemented similar to the electronic processor 14 and the memory 18 as described above. The storage transceiver 66 enables communication from the pharmaceutical storage and retrieval system 30 to the communication network 46. In other embodiments, rather than the storage transceiver 66, the pharmaceutical storage and retrieval system 30 may include separate transmitting and receiving components, for example, a transmitter and a receiver. The pharmaceutical storage and retrieval system 30 through the communication network 46 may communicate with the pre-counter 34, the automatic packager 38, and databases, for example, the National Drug Code database 50.

The storage input/output interface 82 may include one or more input mechanisms (e.g., a touch screen, a keypad, a button, a knob, and the like), one or more output mechanisms (e.g., a display, a printer, a speaker, and the like), or a combination thereof. The storage input/output interface 82 receives input from the input devices actuated by a user, and provides output to the output devices with which a user interacts. In some embodiments, as an alternative or in addition to managing inputs and outputs through the storage input/output interface 82, the pharmaceutical storage and retrieval system 30 may receive user inputs, provide user outputs, or both by communicating with an external device, such as a console computer, over a wired or wireless connection.

Figure 4:
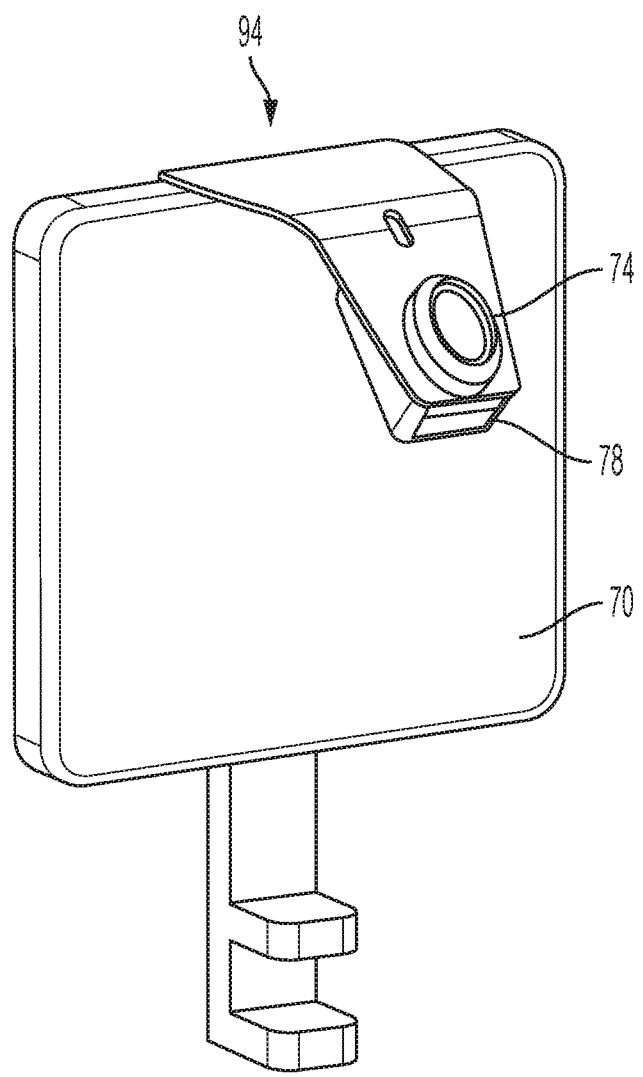
FIG. 4 is a perspective view of a user access assembly of the pharmaceutical storage and retrieval system of FIG. 2 in accordance with some embodiments.

As shown in FIG. 4, the pharmaceutical storage and retrieval system 30 also includes a user authorization system 94. The user authorization system 94 includes the RFID scanner 70, the biometric scanner 74, and the barcode scanner 78. The RFID scanner 70 is integral with the user authorization system 94. In alternate embodiments, the RFID scanner 70 can be separately located proximate the device 54. The biometric scanner 74 is used to identify an authorized user of the system 30 and can be, for example, a fingerprint scanner, an iris reader, a voice recognition scanner, a facial recognition scanner, or combinations thereof.

The barcode scanner 78 can be used to read barcodes such as the NDC on the containers or the labels on custom containers stored in the pharmaceutical storage and retrieval system 30. The barcode scanner 78 can also be used to scan unique barcode labels generated by the system 30 to identify individual containers of particular pharmaceuticals. In such embodiments, the system 30 generates a barcode that is uniquely assigned to each container that is stored in the device 54. As each container is first introduced into the device 54, a label bearing the system 30 generated barcode is affixed to the container. Thereafter each time the container is "checked out" or "checked in" to the system 30, the system 30 cannot only identify the type of medication being "checked out" or "checked in," but can further track the specific container. Accordingly, such embodiments of the system 30 allow multiple containers of the same pharmaceutical or medication to be "checked out" of the system 30 at the same time. Because the system 30 can identify each specific container, the system 30 can associate each container with, for example, a specific operator or a specific prescription order to verify that the order was properly completed.

Referring to FIG. 3, the storage electronic processor 58 may implement a fill prescription module for the pharmaceutical storage and retrieval system 30. In some embodiments, the fill prescription module is operable to retrieve a specific container to fill a customer's prescription from the system 30 using an automated process. In other embodiments, as noted above, the system 30 may be omitted. In such embodiments, a user may manually retrieve the specific container(s) from a location within a pharmacy, such as a closet or shelf. In scenarios where the system 30 is used to retrieve the specific container(s), when the pharmacy receives a prescription to fill, pharmacy personnel enters the information into the pharmacy management system 10, where the pharmacy printer generates an information sheet that includes a list of medications, customer information, and a barcode. The information sheet is taken to the scanner 78 where the barcode is read. At the same time, the user's RFID credential can be read to confirm authorization to the system 30 and the pharmaceuticals stored within. Based on the barcode, the fill prescription module instructs a gantry assembly of the pharmaceutical storage and retrieval device 54 to retrieve the container needed to fill the customer's prescription and identified on the information sheet. More specifically, the fill prescription module communicates with the storage memory 62 to obtain the particular location where the needed container of medication is stored within the device 54. The fill prescription module further communicates the particular location of the container to the gantry assembly so the gantry assembly knows where to go to retrieve the appropriate container. In the instance where a particular container is stored outside the device 54, an external storage location associated with the desired container can be communicated to the operator.

After identifying the particular location of the needed container, the gantry assembly retrieves the container and inserts it into a port 98 of the device 54. After the user's RFID credentials are verified, a front door opens to allow the user to remove the container from the port 98. The pharmacy management system 10 can also communicate the order information directly to the storage electronic processor 58 of system 30, which can direct the device 54 to begin retrieving and staging containers needed for the entered orders. Similar to the process described above, the user can take an information sheet generated by the pharmacy printer to the scanner 78 where the information sheet barcode and the user's RFID are read. If the system 30 recognizes a valid RFID credential and a barcode on the presented information sheet associated with a staged order, the port(s) 74 containing the pharmaceutical(s) needed to fill the order are opened. Accordingly, the system 30 can be configured to retrieve, but not allow access to the needed pharmaceuticals before the information sheet and RFID are scanned.

In scenarios where the system 30 is not present, when the pharmacy receives a prescription to fill, pharmacy personnel may still enter the information into the pharmacy management system 10 where the pharmacy printer generates in an information sheet. In this embodiment, however, the information sheet may not include a barcode to be scanned by a pharmaceutical storage and retrieval system 30. Instead, the information sheet may include a list of medications and customer information. The user may then manually retrieve bulk storage containers containing the desired medications from a storage location (e.g., a closet, a cabinet, a shelf, etc.). Alternatively, the user may directly retrieve the desired bulk storage containers without first entering the information into the pharmacy management system 10 and generating the information sheet.

Figure 5:
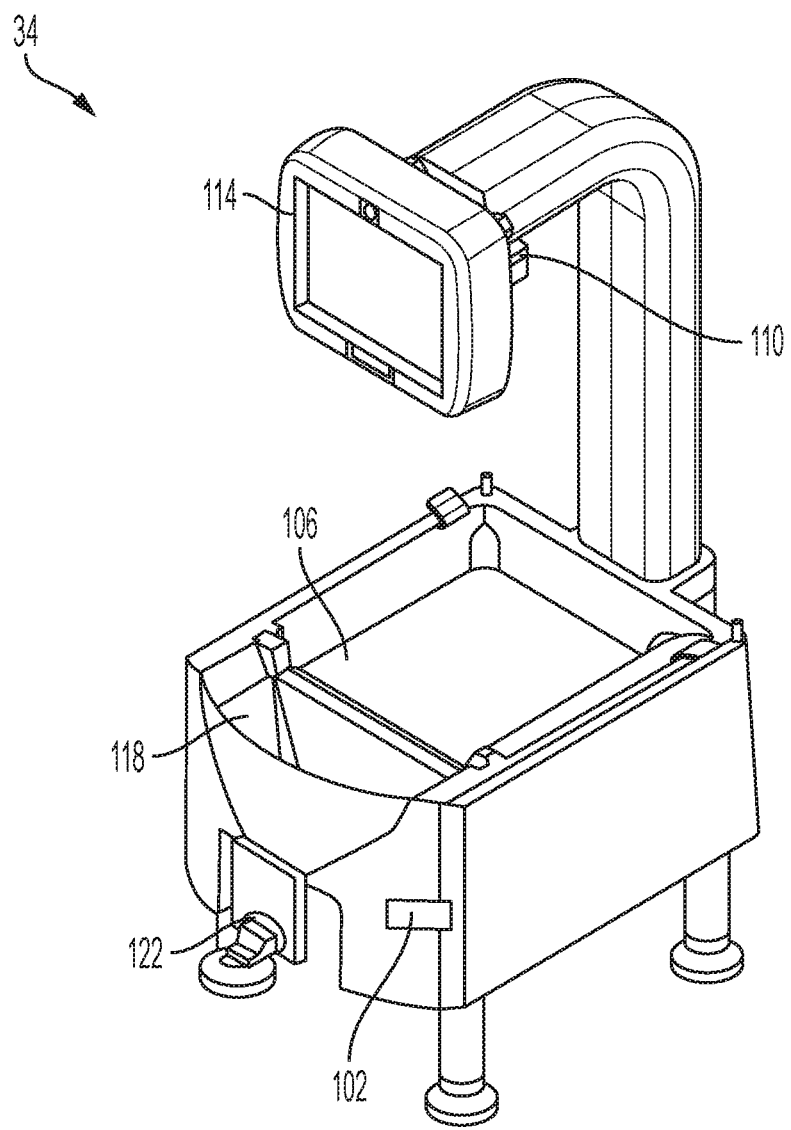
FIG. 5 is a perspective view of a pre-counter for an automatic packager of the pharmacy management system of FIG. 1 in accordance with some embodiments.

FIG. 5 illustrates a pre-counter 34 for the automatic packager 38 according to one example embodiment. The pre-counter 34 is a medication counting device for use in retail pharmacies that detects and counts a number of medications that are placed on the pre-counter 34. The pre-counter 34 displays the count and shares the count with other systems within the pharmacy. As illustrated in FIG. 5, the pre-counter 34 includes a barcode scanner 102, a counting tray 106, a camera system 110, a display 114, a funnel 118, and a funnel gate 122.

The barcode scanner 102 is used to scan a barcode on a label of a container retrieved from the device 54 or other location within the pharmacy and may be implemented similar to the barcode scanner 78. Although the illustrated scanner 102 is identified as a barcode scanner, in other embodiments, the pre-counter may include other types of scanners, such as a scanner for recognizing a Q-code on a bottle or a camera for recognizing an image of or on the bottle. In further embodiments, the scanner 102 may be omitted and a user may directly enter information regarding a bottle into the pre-counter (e.g., a serial number of the bottle via a keypad). The contents of the container may then be placed on the counting tray 106 for counting by the pre-counter 34. The counting tray 106 may be replaceable for cleaning and to inhibit cross-contamination between different types of medications. The counting tray 106 may be transparent or translucent such that a lighting system 126 (see FIG. 6) underneath the counting tray 106 can illuminate the contents of the counting tray 106. Once illuminated, the camera system 110 may capture an image of the contents of the counting tray 106 to commence counting. The display 114 may be used to display the scanned barcode information and to display the count of the medications placed on the counting tray 106. Based on the displayed information, a pharmacist or technician may add or remove medications from the counting tray 106 until the correct amount of medications is placed on the counting tray 106. When the correct amount of medications is placed on the counting tray 106, the user may transfer the contents of the counting tray 106 to a cartridge 158 (FIG. 7) of the automatic packager 38. The funnel 118 and funnel gate 122 are used to transfer the medications from the counting tray 106 to the original container or to the cartridge 158.

Figure 6:
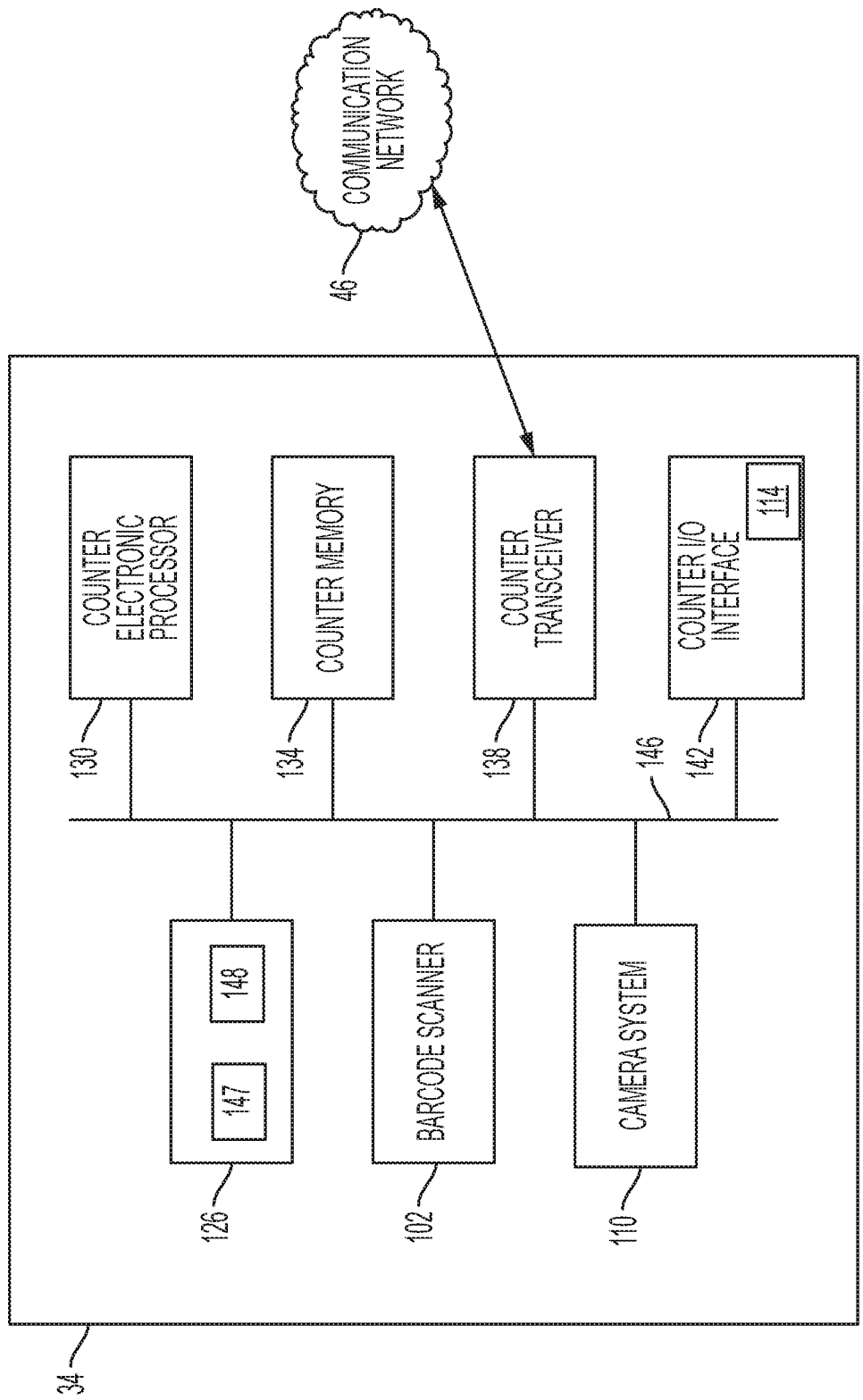
FIG. 6 is a schematic of the pre-counter for an automatic packager of FIG. 5 in accordance with some embodiments.

FIG. 6 schematically illustrates the pre-counter 34 and its functionality within a pharmacy. In the example illustrated, the pre-counter 34 includes a counter electronic processor 130, a counter memory 134, a counter transceiver 138, the barcode scanner 102, the camera system 110, the display 114, the lighting system 126, and a counter input/output interface 142. The counter electronic processor 130, the counter memory 134, the counter transceiver 138, the barcode scanner 102, the camera system 110, the display 114, the lighting system 126, and the counter input/output interface 142 communicate over one or more control and/or data buses (e.g., a communication bus 146). FIGS. 5 and 6 illustrate only one exemplary embodiment of the pre-counter 34. The pre-counter 34 may include more or fewer components and may perform functions other than those explicitly described herein.

The counter electronic processor 130 and the counter memory 134 may be implemented similar to the storage electronic processor 58 and the storage memory 62 as described above. The counter transceiver 138 enables communication from the pre-counter 34 to the communication network 46. In other embodiments, rather than the counter transceiver 138, the pre-counter 34 may include separate transmitting and receiving components, for example, a transmitter and a receiver. The pre-counter 34 through the communication network 46 may communicate with the pharmaceutical storage and retrieval system 30, the automatic packager 38, and databases, for example, the National Drug Code database 50.

The counter input/output interface 142 may include one or more input mechanisms (e.g., a touch screen, a keypad, a button, a knob, and the like), one or more output mechanisms (e.g., a display, a printer, a speaker, and the like), or a combination thereof. The counter input/output interface 142 receives input from the input devices actuated by a user, and provides output to the output devices with which a user interacts. In some embodiments, as an alternative or in addition to managing inputs and outputs through the counter input/output interface 142, the pre-counter 34 may receive user inputs, provide user outputs, or both by communicating with an external device, such as a console computer, over a wired or wireless connection.

The lighting system includes a first light source 147 and a second light source 148. The first light source 147 (e.g., an infrared (IR) or near infrared (NOR) spectrum light) is positioned under the counting tray 106. The first light source 147 shines light through the counting tray 106 toward the camera system 110 to illuminate the contents of the counting tray 106. When the first light source 147 illuminates the counting tray 106, the medications on the counting tray 106 form shadows against a white background of the first light source 147 or the counting tray 106. The camera system 110 captures an image of the shadows cast by the medications on the counting tray 106. The image may be a still image of the medications at a specific instance of time, or may be live image that is continuously transmitted to the display 114. The second light source 148 (e.g., a visible spectrum light) is positioned on the same side of the counting tray 106 as the camera system 110 to shine light on the counting tray 106 and illuminate the contents of the counting tray 106. When the second light source 148 illuminates the counting tray 106, the camera system 110 captures a visible light image of the medications, showing the color, shape, contour, surface finish, etc. of the medications. The image may be a still image of the medications at a specific instance of time, or may be a live image that is continuously transmitted to the display 114. The camera system 110 communicates with the counter electronic processor 130 and the counter memory 134 to store the images and/or transmit the images to the display 114.

Figure 7:
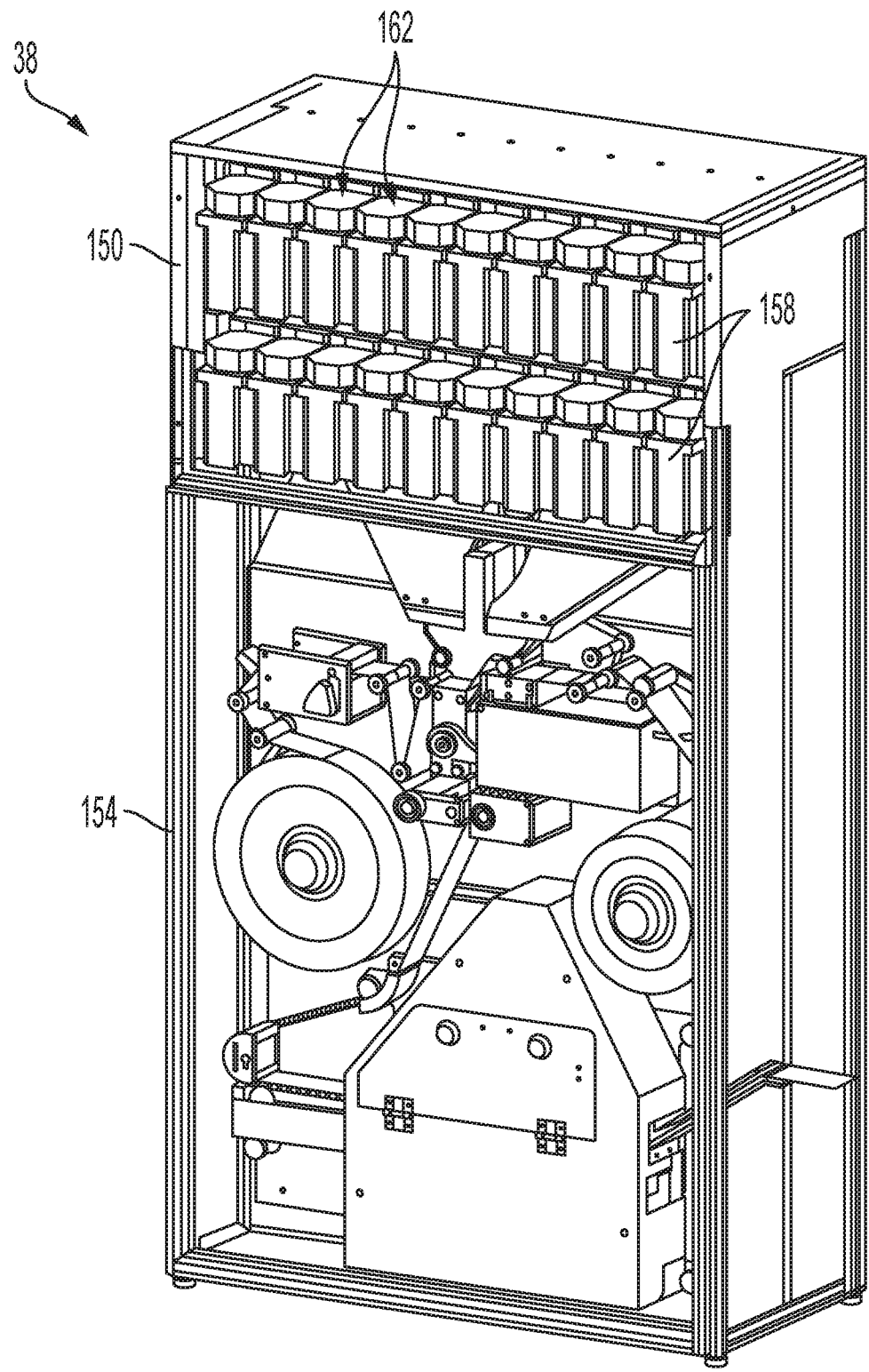
FIG. 7 is a perspective view of an automatic packager of the pharmacy management system of FIG. 1 in accordance with some embodiments.

FIG. 7 illustrates an example automatic packager 38 including a universal feed cassette 150 and a packaging unit 154 according to an example embodiment. The universal feed cassette 150 receives medications from the bulk canisters or the pre-counter 34 and individually dispenses pills to the packaging unit 154. Each universal feed cassette 150 may dispense ten separate pills at the same time. In other embodiments, the universal feed cassette 150 may dispense twenty or more separate pills at the same time. In some embodiments, the automatic packager 38 may include more than one universal feed cassette 150.

The universal feed cassette 150 includes a plurality of cartridges 158 arranged within the housing of the universal feed cassette 150. In one example, the universal feed cassette 150 may include up to ten cartridges 158 that are received in cartridge slots 162. In another example, the universal feed cassette 150 may include up to twenty cartridges 158 that are received in the cartridge slots 162. For example, the cartridges 158 may be received in two levels or tiers of cartridge slots 162. A pharmacist may load medications from bulk canisters or the pre-counter 34 into each of the cartridges 158. The same medications may be loaded into each cartridge 158, or different medications may be loaded into each cartridge 158. The cartridges 158 independently dispense the medications to the packaging unit 154.

The cartridges 158 are removably fixed to the universal feed cassette 150. A pharmacist or technician may remove each individual cartridge 158 from the cartridge slot 162 to fill the cartridge 158 with medications from the pre-counter 34. The cartridge 158 can then be placed into any of the cartridge slot 162.

An example cartridge 158 is described in U.S. patent application Ser. No. 16/160,535, filed on Oct. 15, 2018, entitled "UNIVERSAL FEED MECHANISM FOR AUTOMATIC PACKAGER," the entire contents of which are hereby incorporated by reference. In other embodiments, other suitable cartridges may also or alternatively be used. In the example illustrated in FIG. 7, the packaging unit is a strip packager. An example strip packager is described in U.S. Patent Application Publication No. 2013/031891 and U.S. Patent Application Publication No. 2017/0015445, the entire contents of both of which are hereby incorporated by reference. In other embodiments, other suitable packaging units, including strip packagers, blister card packagers, and the like, may also or alternatively be used.

Figure 8B:
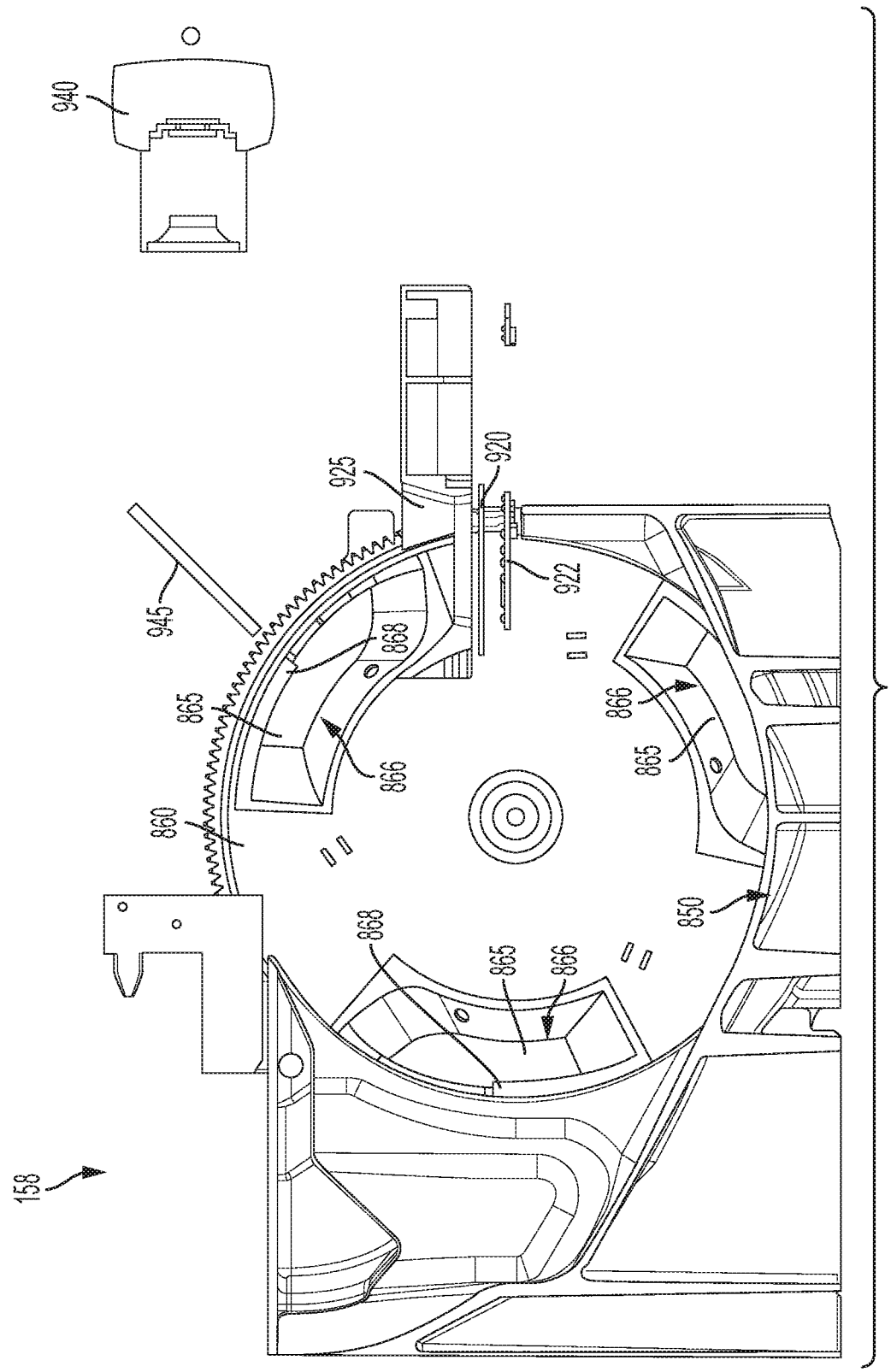
FIG. 8B is a plan view of the cartridge of FIG. 8A with a side portion removed in accordance with some embodiments.
Figure 8C:
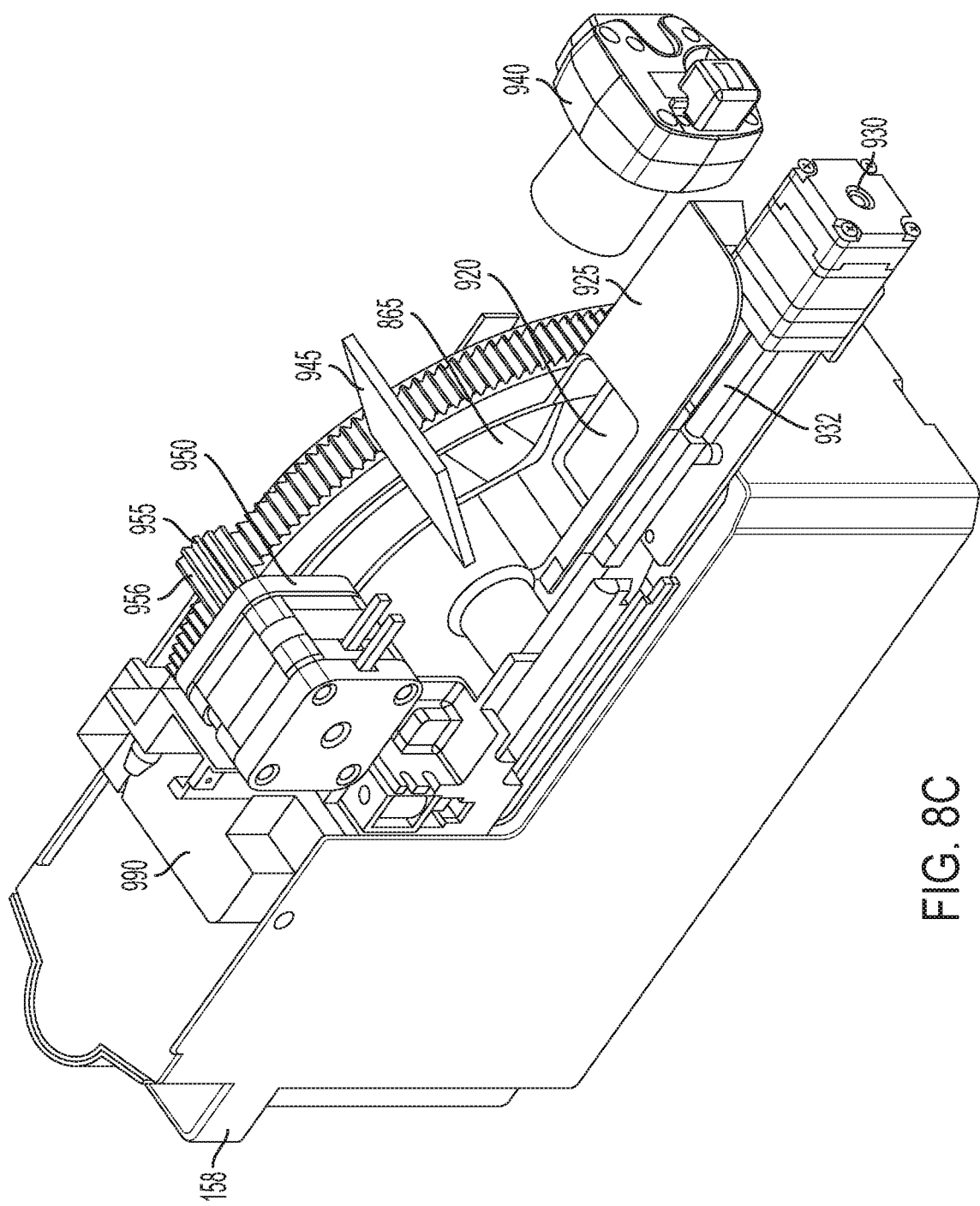
FIG. 8C is a perspective view of the cartridge of FIG. 8A in accordance with some embodiments.

FIGS. 8A-C illustrates one example embodiment of the cartridge 158. In the example illustrated, the cartridge 158 includes a reservoir 850, a wheel 860, and scooping members 865. The reservoir 850 stores the medications during the dispensing process. The wheel 860 is provided on one side of the cartridge 158 and extends into the bottom portion of the reservoir 850. The bottom portion of the reservoir 850 has a curved shape starting from the side opposite that of the wheel 860, the front side, and the back side and ending at the center of the bottom portion of the wheel 860. The curved shape of the reservoir 850 directs the medications within the reservoir 850 towards the bottom of the wheel 860 and particularly into the scooping members 865 of the wheel 860.

Teeth 875 are provided on the outer circumferential surface of the wheel 860. During the dispensing process, the teeth 875 interlock with teeth of a shaft driven by a motor assembly of the cartridge mechanism 845. The wheel 860 is provided with three scooping members 865 to scoop individual medications from the reservoir 850. The scooping members 865 include an inward projection 866 extending into the wheel 860. The curved surface of the reservoir 850 guides the medications into the inward projections 866 of the scooping members 865. The scooping members 865 include a stopper 868 along a circumferential end of the inward projections 866 that hold the medications when the wheel 860 is being rotated.

The wheel 860 includes holding pins 880 that extend and retract from the inside of the wheel 860 during rotation of the wheel 860. The scooping members 865 include an opening to receive the holding pins 880. The holding pins 880 along with the stopper 868 and the circumferential surface of the inward projection 866 are used to hold a medication when the wheel 860 is being rotated. During rotation of the wheel 860, when the inward projections 866 of the scooping members 865 encounter the reservoir 850, the medications in the reservoir 850 move inward into the scooping members 865 due to the curved shape of the reservoir 850. The holding pins 880 are retracted when the scooping members 865 are moving along the reservoir 850 at a bottom portion of the wheel 860. As the scooping members 865 move out of the reservoir 850, the holding pins 880 are advanced towards the circumferential end of the scooping members 865 to engage a medication. The medications are held between the circumferential end of the scooping member 865, the holding pin 880, and the stopper 868. The scooping member 865 and the holding pin 880 can be used for any type of medication. Typically, only a single medication is pinched between the holding pin 880 and the scooping member 865, while the other medications fall back into the reservoir 850 during the rotation of the wheel 860. As the scooping member 865 passes the top portion of the wheel 860, the holding pin 880 is once again retracted to release the medication into a shuttle system. The wheel 860 and the scooping member 865 may together be referred to as a singulating mechanism.

The cartridge 158 also includes a shuttle system, a camera system, and a motor assembly. The shuttle system includes a platform 920, a shuttle 925, and a shuttle drive 930. The platform 920 may be made from a clear or translucent plastic material. An LED lighting system 922 may be provided over and/or under the platform 920 to illuminate the contents on the platform 920 when the camera system is capturing an image of the contents. The LED lighting system 922 may emit visible or infrared light to illuminate the platform 920. The shuttle 925 may be moved laterally between the platform 920, over the reservoir 850, and over a conduit. The shuttle 925 transfers the medications from the platform 920 either to the reservoir 850 or to the conduit. The shuttle 925 is driven by the shuttle drive 930. The shuttle drive 930 may be a motor assembly, an actuator, or the like that moves the shuttle 925 between the platform 920, over the reservoir 850, and over the conduit. In the example illustrated, the shuttle drive 930 includes a rotating screw 932 that moves the shuttle 925 laterally between the platform 920, the reservoir 850, and the conduit.

The camera system includes a camera 940 and a mirror 945. The camera 940 is positioned at the back of the cartridge mechanism 845. The camera 940 may be a still camera or a video camera that captures an image of the contents of the platform 920. The mirror 945 is placed directly above the platform 920 and is tilted at a 45-degree angle such that the camera 940 positioned at the back of the cartridge mechanism 845 can capture an image of the platform 920.

In some embodiments, the camera system is operable in a learning mode to create a database of images of medications currently in the cartridge 158. For example, as each medication is singulated by the wheel 860, the camera 940 captures an image of the medication, the image is stored in a database, and the shuttle 925 returns the medication to the reservoir 850. This process may be repeated, for example, 50-100 times to capture images of the medications in different orientations.

The motor assembly includes a motor 950 that drives a shaft 955 positioned in the middle of the cartridge mechanism 845. The shaft 955 includes teeth 956 that interlock with the teeth 875 of the wheel 860. When the motor 950 is driven, the shaft 955 rotates the wheel 860 to the individually dispense the medications 180.

The cartridge 158 may include an RFID tag that may be used to identify the cartridge 158. The RFID tag may be read by an RFID reader of the pre-counter 34 or the automatic packager 38.

Figure 9:
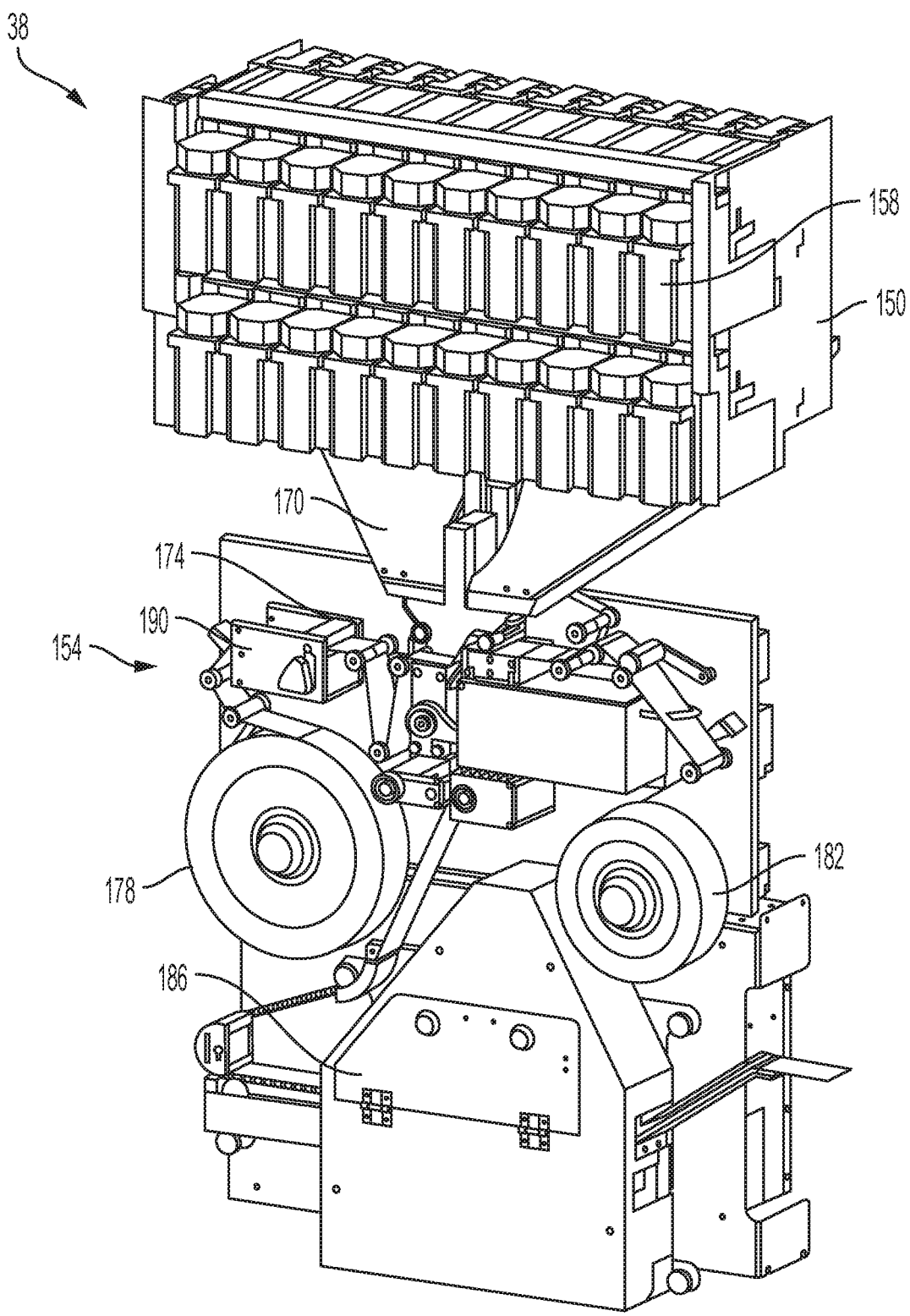
FIG. 9 is a plan view of a packaging unit of the automatic packager of FIG. 7 in accordance with some embodiments.

FIG. 9 illustrates one embodiment of the packaging unit 154. In the example illustrated, the packaging unit 154 includes a manifold 170, a receptacle 174, two feed stock rolls 178, 182, a take-up roll, and a verification system 186. The universal feed cassette 150 is placed on top of the manifold 170. The manifold 170, or chute, includes a plurality of discrete tracks corresponding to each of the cartridges 158 (particularly, a conduit of each cartridge 158) mounted on the manifold 170. The illustrated tracks are independent channels that together form the manifold 170. The tracks direct pharmaceuticals from the universal feed cassette 150 toward packaging equipment of the packaging unit 154. Conduits of the cartridges 158 align with holes in the manifold 170 such that medications slide down the manifold 170 toward the packaging equipment. The tracks 190 isolate the medications from each other as the medications slide down the manifold 170 to the receptacle 174.

The receptacle 174 collects the medications from the manifold 170. After the medications pass through to the receptacle 174, the medications are sandwiched between two strips of material (e.g., plastic, paper, etc.) from the feed stock rolls 178, 182. The first feed roll 178 may be made of a first material that is white in color (e.g., a translucent material). The second feed roll 182 may be made of a second material that is clear (e.g., a transparent material) to allow a pharmacist to look through the pouch to see the medications inside the pouch. The two strips of material are then heat sealed together to form a pouch for the medications. In some embodiments, the packaging unit 154 may include a single feed stock roll having a single strip of material that is folded and/or heat sealed to form pouches. Once filled and sealed, the pouches are wrapped around the take-up roll to create a single spool of pouches. The spool may correspond to medications requested by a particular patient or a particular facility. In other embodiments, the pouches may be cut and separated as they are filled, rather than spooled onto the take-up roll continuously. The pouches are dispensed through, for example, a dispenser or dispensing port connected.

In some embodiments, the packaging unit 154 may include a printer 194 to print a patient's name, the date, the amount and type of medications contained within, a barcode, and/or other indicia on the pouches as the pouches are formed. The printer 194 may be, for example, a thermal printer. In other embodiments, the printer 194 may include an ink ribbon or an ink jet. In addition, the packaging unit 154 may include a verification system 186 to monitor and check the pouches as they are spooled onto the take-up roll or dispensed.

Figure 10:
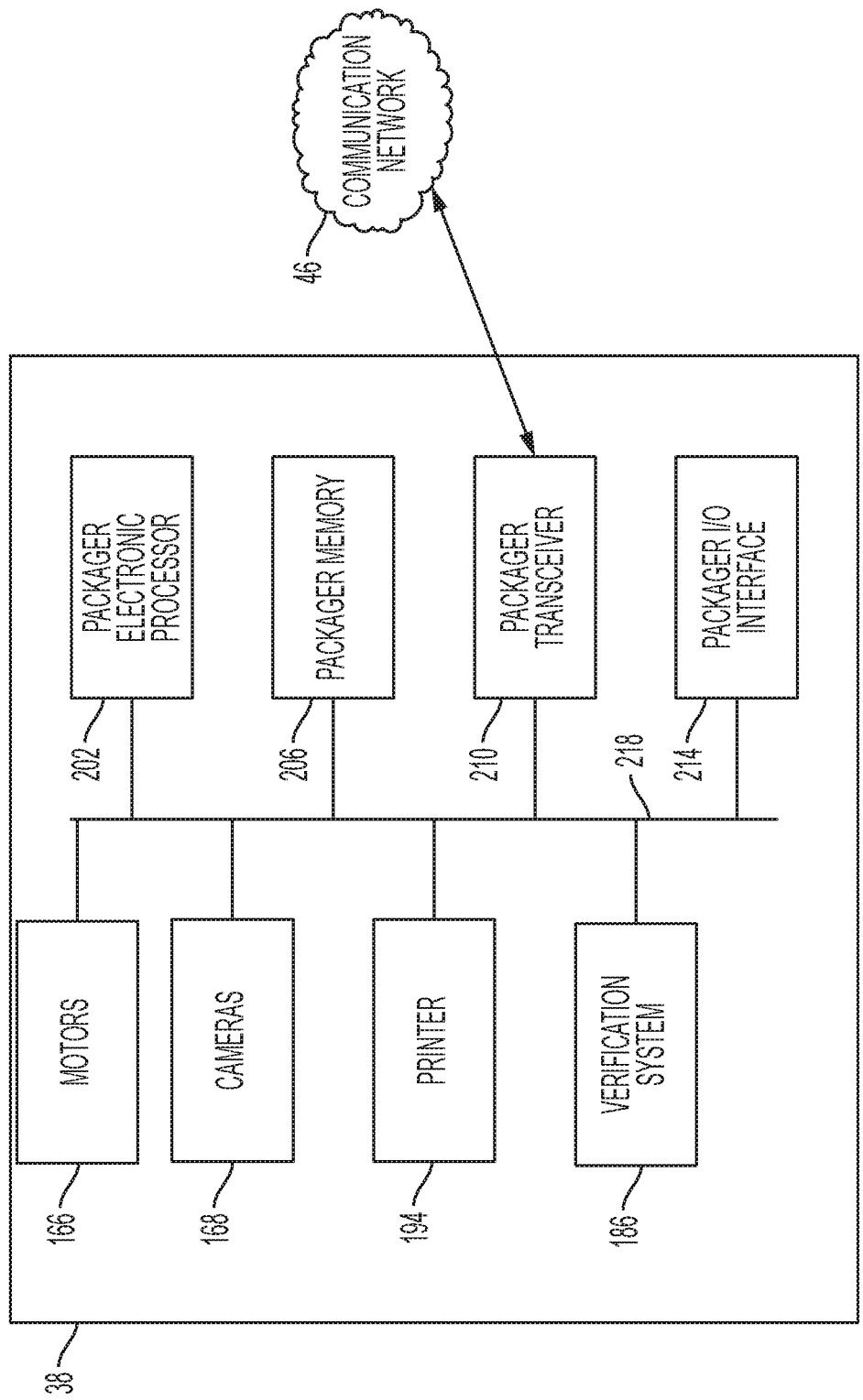
FIG. 10 is a schematic of the automatic packager of FIG. 7 in accordance with some embodiments.

FIG. 10 schematically illustrates one embodiment of the automatic packager 38. The automatic packager 38 controls operations of the feed stock rolls 178, 182 to release and form a pharmaceutical pouch, and controls when the active cartridges 158 positioned on the manifold 170 are operated.

In the example illustrated, the automatic packager 38 includes a packager electronic processor 202, a packager memory 206, a packager transceiver 210, a packager input/output interface 214, the motors 166, the cameras 168, the printer 194, and the verification system 186. The packager electronic processor 202, the packager memory 206, the packager transceiver 210, the packager input/output interface 214, the motors 166, the cameras 168, the printer 194, and the vision system 198 communicate over one or more control and/or data buses (e.g., a communication bus 218). FIG. 10 illustrates only one exemplary embodiment of the automatic packager 38. The automatic packager 38 may include more or fewer components and may perform functions other than those explicitly described herein.

The packager electronic processor 202 and the packager memory 206 may be implemented similar to the storage electronic processor 58, the counter electronic processor 130, the storage memory 62, and the counter memory 134 respectively, as described above. The packager transceiver 210 enables communication from the automatic packager 38 to the communication network 46. In other embodiments, rather than the packager transceiver 210, the automatic packager 38 may include separate transmitting and receiving components, for example, a transmitter and a receiver. The automatic packager 38, through the communication network 46, may communicate with the pharmaceutical storage and retrieval system 30, the pre-counter 34, and databases, for example, the National Drug Code database 50.

As noted above, the automatic packager 38 may include the packager input/output interface 214 (or more commonly referred to as a user interface). The packager input/output interface 214 may include one or more input mechanisms (e.g., a touch screen, a keypad, a button, a knob, and the like), one or more output mechanisms (e.g., a display, a printer, a speaker, and the like), or a combination thereof. The packager input/output interface 214 receives input from the input devices actuated by a user, and provides output to the output devices with which a user interacts. In some embodiments, as an alternative or in addition to managing inputs and outputs through the packager input/output interface 214, the automatic packager 38 may receive user inputs, provide user outputs, or both by communicating with an external device, such as a console computer, over a wired or wireless connection.

One advantage of the cartridges 158 is that the cartridges 158 significantly reduce the packaging time compared to prior cartridges. Some prior cartridges had to be manually filled one pill at a time by a pharmacist or a technician. In contrast, the pharmacist or technician may simply dump pills from a bulk container into the cartridge 158 and place the cartridge 158 in the universal feed cassette 150. The automatic packager 38 then retrieves medications from the cartridge 158. Typically, a pharmacist or technician may have to overfill the cartridge 158 to ensure that sufficient medications are available in the cartridge 158 to fill the prescription without having to refill the cartridge 158. Once the medications are packaged, the pharmacist or technician returns the unused medications to the bulk container. However, this introduces an inefficiency into the system 10 where the bulk container needs to be outside the storage area until the packaging process is completed to receive any excess medications from the cartridges 158. The pre-counter 34 helps overcome this inefficiency by allowing a pharmacist to quickly and efficiently count the exact number of pills required to fill the prescription and return the bulk container to storage.

Figure 11:
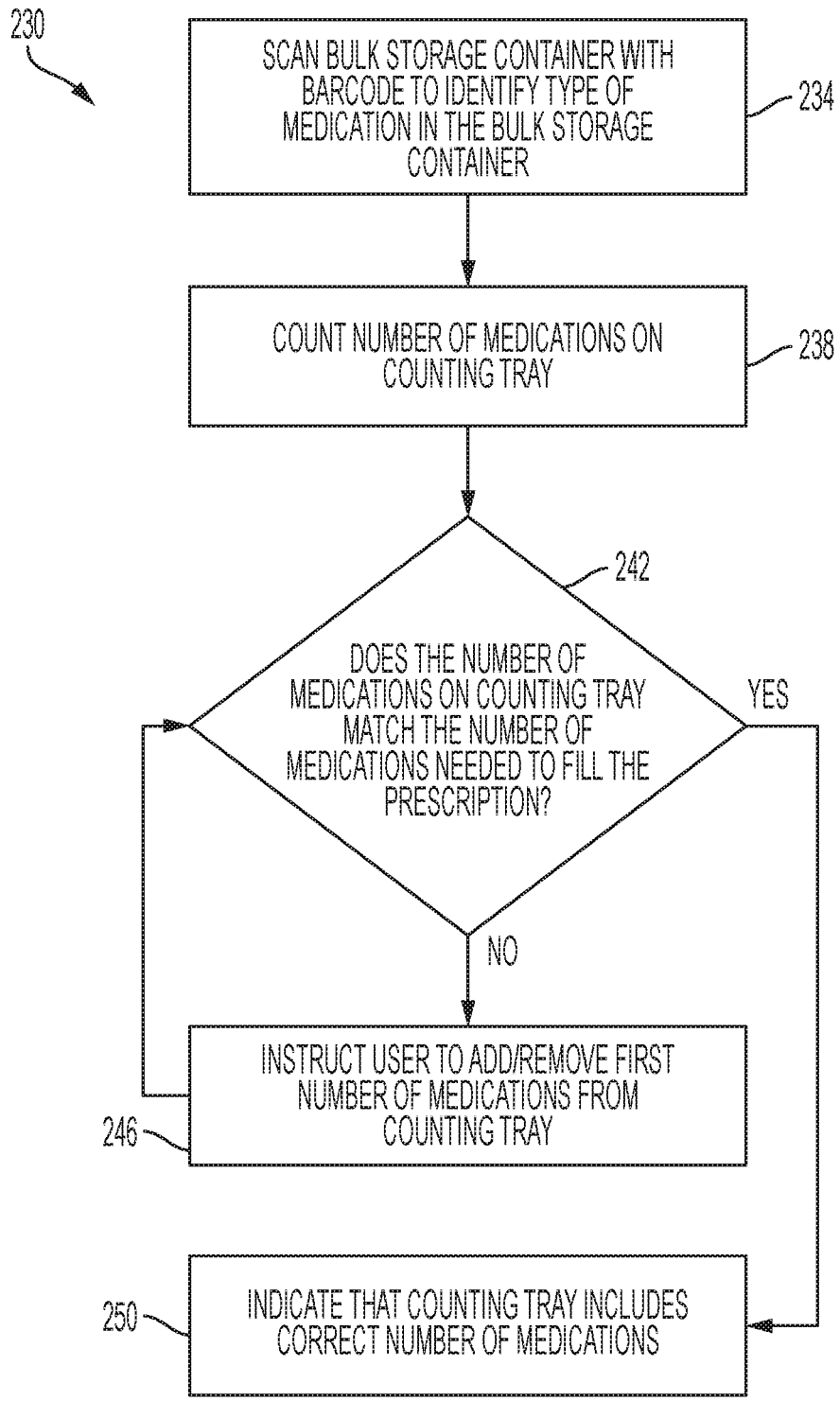
FIG. 11 is a flowchart of a method of pre-counting medications for filling a prescription in accordance with some embodiments.

FIG. 11 depicts a method 230 of pre-counting medications for filling a prescription. Although the method 230 includes specific blocks, all the blocks need not be performed or performed in the order presented. When the pharmacist receives a prescription from a customer, the pharmacy management system 10 generates an information sheet including a list of all the medications required to fill the prescription. The pharmacist uses the information sheet to retrieve bulk containers including the medications in the information sheet. For example, the pharmacist retrieves the bulk container from the pharmaceutical storage and retrieval system 30 or from storage shelves in the pharmacy.

At block 234, the method 230 includes scanning, using the counter electronic processor 130 with the barcode scanner 102, a bulk storage container with a barcode to identify the type of medication in the bulk storage container. Once the pharmacist retrieves the bulk storage containers, the pharmacist scans the bulk storage containers at the pre-counter 34. The barcode scanner 102 scans the barcode on the bulk storage containers and provides the identification information read from the barcode to the counter electronic processor 130. The counter electronic processor 130 retrieves information pertaining to the medication within the bulk storage container using the identification information. For example, the counter electronic processor 130 communicates with the NDC database 50 to determine the type, the weight, the size, the color, etc. of the medication within the bulk storage container. Scanning the bulk storage containers at the pre-counter 34 also verifies that the correct bulk storage containers were retrieved.

At block 238, the method 230 includes counting, using the counter electronic processor 130 with the camera system 110, the number of medications on the counting tray 106 of the pre-counter 34. After scanning a bulk storage container, the pharmacist pours medications from the bulk storage container onto the counting tray 106. The counter electronic processor 130 activates the first light source 147 to illuminate the counting tray 106 and continuously captures an image of the counting tray 106 using the camera system 110 to determine the number of medications on the counting tray 106. In some embodiments, the first light source 147 may always be turned on when the pre-counter 34 is turned on. As described above, the first light source 147 is an IR or a NIR light source that cast shadows of the medications against a white background. The counter electronic processor 130 processes the image captured by the camera system 110 using known image processing systems to determine the number of medications on the counting tray 106. Particularly, the counter electronic processor 130 analyzes the shadows cast by the medications to determine the number of medications on the counting tray 106. In some embodiments, the pre-counter 34 continuously captures the image of the counting tray 106 at regular time intervals (e.g., every 0.5 seconds) to update the count of the medications.

At block 242, the method 230 determines whether the number of medications on the counting tray 106 matches the number of medications needed to fill the prescription. The pre-counter 34 may receive the prescription information or the label sheet information from the pharmacy management system 10. The pre-counter 34 determines the number of medications needed to fill the prescription from the prescription information or the label sheet information. Particularly, the pharmacist may scan the information sheet generated by the pharmacy management system 10 using the bar code scanner 102. The pharmacy management system 10 sends the information included on the information sheet to the pre-counter 34. The electronic processor 14 of the pharmacy management system 10 communicates with the pre-counter 34 using the transceiver 22 and the communication network 46 to provide the information on the information sheet to the counter electronic processor 130. The counter electronic processor 130 retrieves the information received from the pharmacy management system 10 based on scanning the bar code on the information sheet. The pre-counter 34 compares the number of medications on the counting tray 106 to the number of medications needed to fill the prescription.

When the number of medications on the counting tray 106 does not match the number of medications needed to fill the prescription, the pre-counter 34 instructs the user to add/remove a first number of medications from the counting tray 106, at block 246. The pre-counter 34 determines the difference between the number of medications on the counting tray 106 and the number of medications needed to fill the prescription and indicates to the user (e.g., using the display 114) to add or remove the first number of medications corresponding to the difference between the number of medications on the counting tray 106 and the number of medications needed to fill the prescription. For example, if 30 medications are needed to fill the prescription, but 32 medications are poured onto the counting tray 106, the pre-counter 34 instructs the user to remove 2 pills and return the pills to the bulk container. Conversely, if 30 medications are needed to fill the prescription, but 28 medications are poured onto the counting tray 106, the pre-counter 34 instructs the user to add 2 pills to the counting tray 106 from the bulk container. As described above, the method 230 then returns to block 242 to continuously determine the number of medications on the counting tray 106.

When the number of medications on the counting tray 106 match the number of medications needed to fill the prescription, the pre-counter 34 indicates that the counting tray 106 includes the correct number of medications, at block 250. The pre-counter 34 may also process the images captured to identify whether any medications are broken or whether the counting tray 106 includes any debris. The pre-counter 34 instructs the pharmacist to remove the broken medications or debris from the counting tray 106. The pharmacist then empties the medications on the counting tray 106 into one of the cartridges 158. The method 230 is repeated for each medication in the prescription to fill different ones of the cartridges 158. This allows the pharmacist to fill the exact number of medications needed to fill the prescription into the cartridges 158 and does not need to dump excess medications from the cartridges 158 back into the bulk storage container after packaging.

In addition to counting the number of medications, the pre-counter 34 may also be used to determine one or more characteristics of the medications. For example, the pre-counter 34 may be used to determine the color and dimensions of the medications. The NDC information received from the NDC database 50 generally includes information regarding the color and size of the medications within set ranges. The pharmacy management system 10 communicates the color and size information with the automatic packager 38 for verification during dispensing and while packaging. However, there may be variations in the shade of the color (e.g., shade of blue) and size during manufacturing. For example, when manufacturing the medications, the medications do not always come out with the same color quality. A medication may be identified as blue in the database, but the shade of blue may be slightly different in the actual medication. Similarly, a medication may be identified in the database as having a diameter of 2 to 3 millimeters, and the actual size of the medication may be anywhere within that range.

As described above, the pre-counter 34 is used to capture an image of the medications in the IR/NIR, and visible light spectrum using the camera system 110 to determine one or more characteristics of the medications. For example, the counter electronic processor 130 activates the second light source 148 and captures an image of the counting tray 106 including the medications using the camera system 110. The counter electronic processor 130 processes the image captured by the camera system 110 using known image processing techniques to determine the actual color (e.g., a particular shade of color) of the medications. Similarly, the counter electronic processor 130 processes the image captured by the camera system 110 to determine the actual size (e.g., a measured size) of the medications. The counter electronic processor 130 can determine if the actual color and actual size are within the ranges of expected color and expected size provided by the NDC database 50. The pre-counter 34 correlates the color information and the size information with the identification information of the medication determined after scanning the barcode of the bulk storage container. The pre-counter 34 transmits the color information and the size information for each medication in the prescription to the automatic packager 38 and/or the pharmacy management system 10. In some embodiments, the pre-counter 34 may only measure one characteristic (e.g., color or size) associated with each medication. In further embodiments, the pre-counter 34 may also or alternatively determine and compare other characteristics of the medications, such as weight (e.g., via a scale integrated into the counting tray 106), shape, and the like.

Figure 12:
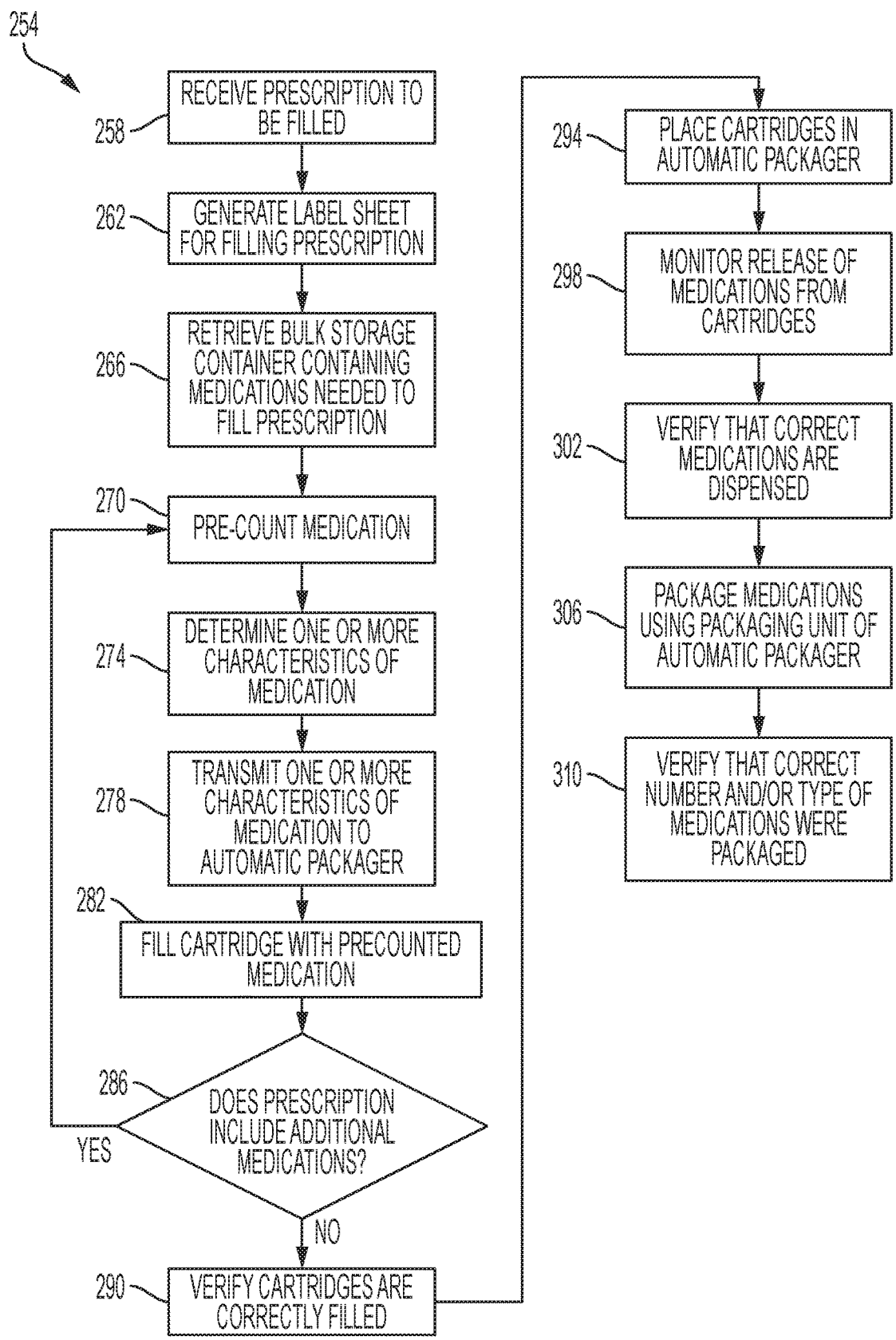
FIG. 12 is a flowchart of a method of filling a prescription in accordance with some embodiments.

FIG. 12 depicts a method 254 for filling a prescription in a pharmacy. Although the method 254 includes specific blocks, all the blocks need not be performed or performed in the order presented. The pharmacy is an automated pharmacy including the pharmaceutical storage and retrieval system 30, the pre-counter 34, and the automatic packager 38 as described above. As noted above, the pharmaceutical storage and retrieval system 30 may be omitted. The method 254 leverages the automated nature of the pharmacy to verify the correct type and/or number of pharmaceuticals are loaded into each pouch as part of filling the prescription. In particular, the method 254 involves providing a triple verification system for a pharmacist to verify filling the prescription from when the prescription is received until the pharmaceuticals are loaded and sealed in a pouch to create a chain of custody for the pharmaceuticals. The chain of custody may be stored as an electronic file in the memory 18 of the pharmacy management system 10 or a remote computer or server.

At block 258, the method 254 includes receiving, at the electronic processor 14, a prescription to be filled by the pharmacy management system 10. In one embodiment, the prescription may be received electronically through the communication network 46 from a healthcare facility. In other embodiments, the prescription may be received by scanning a paper prescription presented by a customer or by manually entering the contents of the prescription presented by the customer into the pharmacy management system 10.

At block 262, the method 254 includes generating, with the electronic processor 14, an information sheet for filling the prescription. Generating the information sheet may include the pharmacy management system 10 electronically generating a list of medications (for example, including identifying information of the medications) provided in the prescription and transmitting the information sheet to the pharmaceutical storage and retrieval system 30, the pre-counter 34, and/or the automatic packager 38. In other embodiments, the pharmacy management system 10 prints the information sheet using a pharmacy printer. The pharmacist may then physically carry the information sheet to be scanned by the pharmaceutical storage and retrieval system 30, the pre-counter 34, and/or the automatic packager 38.

At block 266, the method 254 includes retrieving bulk storage containers containing the medication needed to fill the prescription. As described above, the pharmaceutical storage and retrieval system 30 retrieves the containers including the medications for the prescription to be picked up by the pharmacist in response to receiving or scanning the information sheet at the pharmaceutical storage and retrieval system 30. In other embodiments, the pharmacist may manually retrieve the containers including the medications from storage shelves of the pharmacy based on the information sheet.

At block 270, the method 254 includes pre-counting, using the pre-counter 34, the medications needed to fill the prescription. A method for pre-counting the medication is described above with respect to FIG. 11. At block 274, the method 254 includes determining, using the pre-counter 34, one or more characteristics of the medications needed to fill the prescription. The one or more characteristics may include a shape, dimensions, or color(s) of the medications. The one or more characteristics may be determined using the camera system 110 described above. At block 278, the method 254 includes transmitting, using the pre-counter 34, the one or more characteristics of the medications to the automatic packager 38. The pre-counter 34 transmits the one or more characteristics to the automatic packager 38 over the communication network 46.

At block 282, the method 254 includes filling the cartridge 158 with the pre-counted medication. Once the required number of medications is placed on the counting tray 106, the pharmacist fills a cartridge 158 by emptying the counting tray 106 into the cartridge 158 using the funnel 118 and the funnel gate 122. At block 286, the method 254 includes determining whether the prescription includes additional medications to be processed. The pre-counter 34 counts and determines the one or more characteristic for each type of medication needed to fill the prescription. When the pharmacy management system 10 determines that there are additional medications to be processed, the method 254 returns to block 270 to process the next medication in the prescription. When the pharmacy management system 10 determines that all the medications in the prescription are processed and filled into the cartridges 158, the method proceeds to block 290.

At block 290, the method 254 includes verifying that the cartridges 158 are correctly filled. As described above, the pre-counter 34 provides the one or more characteristics of the medications to the pharmacy management system 10. The pre-counter 34 may also provide identifying information along with an image (e.g., from the captured images) and a final count (e.g., before the counting tray 106 is emptied) of the medications to the pharmacy management system 10. The pharmacy management system 10 receives the information from the pre-counter 34 and displays the information on a display of the pharmacy management system 10 for verification by the pharmacist. In one example, the pharmacy management system 10 compares the image of the medication received from the pre-counter 34 to an image available on, for example, the NDC database 50. The pharmacy management system 10 may also display the image received from the pre-counter 34 side-by side with the image available on the NDC database 50 for verification by the pharmacist. The pharmacy management system 10 may indicate whether the correct medications were filled in the cartridges 158 to a user. The indication may include providing a colored border around an image of each medication. This provides an opportunity for the pharmacist to correct any errors prior to the medications being packaged.

At block 294, the method 254 includes placing the cartridges 158 in the automatic packager 38. The filled cartridges 158 are placed in cartridge slots 162 of the automatic packager 38 to begin packaging the medications. At block 298, the method 254 further includes monitoring, using the automatic packager 38, release of medications from the cartridges 158. As described above, the automatic packager 38 includes sensors and cameras 168 in the cartridges 158 to count and capture images while the medications are being dispensed from the cartridges 158. The automatic packager 38 may provide the count and the images to the pharmacy management system 10.

At block 302, the method 254 includes verifying, using the automatic packager 38, that the correct medications are dispensed. The automatic packager 38 verifies that the correct medications are dispensed by comparing an image captured by the cameras 168 with the image of the medication received from the pre-counter 34. The automatic packager 38 may provide the captured image and the image received from the pre-counter 34 for display at the pharmacy management system 10. The automatic packager 38 may additionally provide an indication of whether the correct medications are dispensed by providing a colored border around the images as described above. This provides a second opportunity for the pharmacist to correct any errors prior to the medications being packaged.

At block 306, the method 254 includes packaging the medications using the packaging unit 154 of the automatic packager 38. As described above, the medications may be packaged into pouches or strip packages to be provided to a customer. At block 310, the method 254 includes verifying that the correct number and/or type of medications were packaged into the pouches or strip packages. An example method of verifying the correct number and/or type of pharmaceuticals in a pouch or strip package is described in U.S. Patent Application Publication No. 2018/0091745, filed Sep. 27, 2016, entitled "VERIFICATION SYSTEM FOR A PHARMACY PACKAGING SYSTEM," the entire contents of which are hereby incorporated by reference. In some embodiments, packaging includes sealing the medications in a pouch, a blister card, a vial, or other suitable packages. The automatic packager 38 uses the verification system 186 to capture images of the pouches. The automatic packager 38 verifies that the correct number and/or type of pharmaceuticals were packaged by comparing the image captured by the verification system 186 with the image of the medication received from the pre-counter 34. The automatic packager 38 may provide the captured image and the image received from the pre-counter 34 for display at the pharmacy management system 10. The automatic packager 38 may additionally provide an indication of whether the correct medications are packaged by providing a colored border around the images as described above. Accordingly, the method 254 provides a third opportunity for a pharmacist to correct any errors before providing the packaged medications to the customer.

One advantage of the above methods is that a pharmacist is provided with three opportunities to ensure the prescription is accurately filled. Additionally, the above methods leverage the automated pharmacy to efficiently package pharmaceuticals such that customer wait times are reduced.

Figure 13:
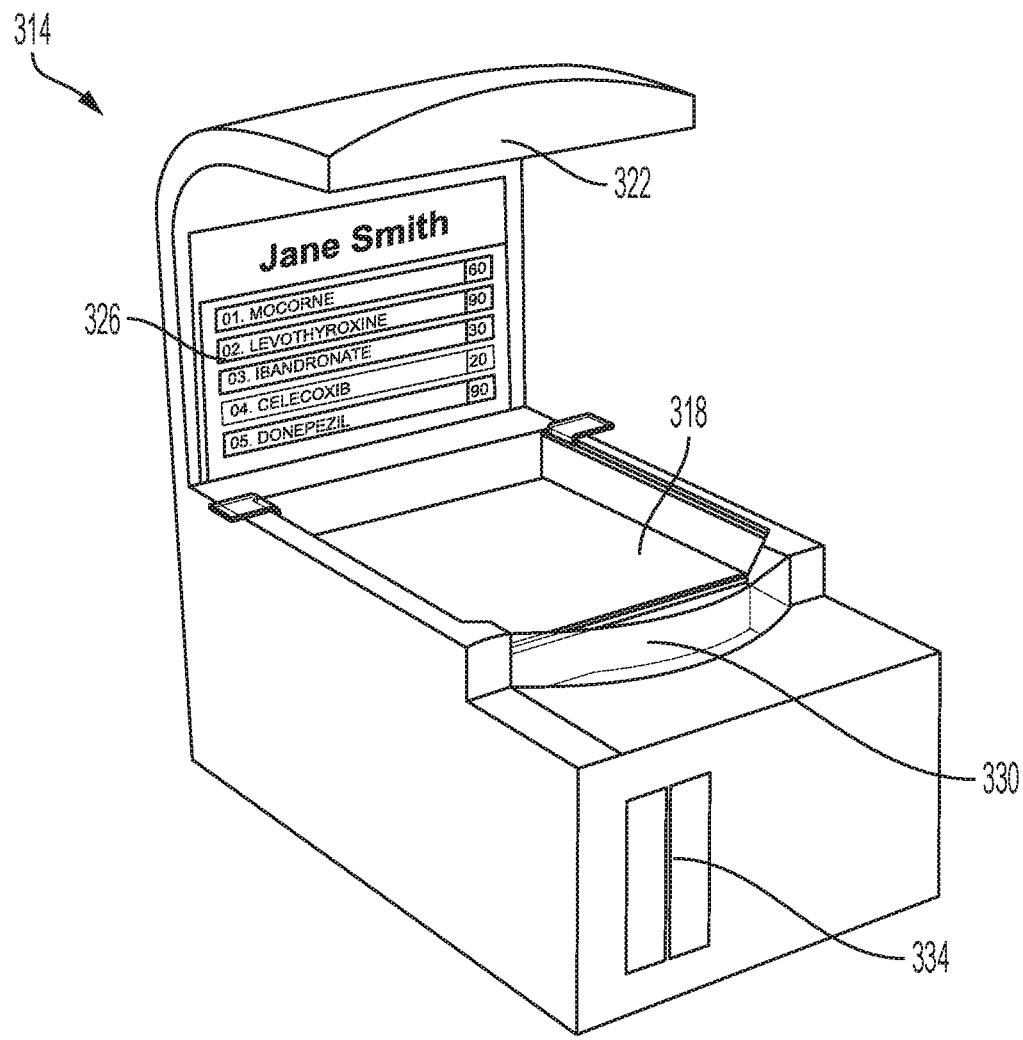
FIG. 13 is a perspective view of a pre-counter for an automatic packager of the pharmacy management system of FIG. 1 in accordance with some embodiments.

FIG. 13 illustrates a pre-counter 314 for the automatic packager 38 according to another example embodiment. The pre-counter 314 is a medication counting device for use in retail pharmacies that detects and counts a number of medications that are placed on the pre-counter 314. The pre-counter 314 displays the count and shares the count with other systems within the pharmacy. As illustrated in FIG. 13, the pre-counter 314 includes a counting tray 318, a camera system 322, a display 326, a funnel 330, and a cartridge slot 334.

The camera system 322 includes a barcode scanner 102 (see FIG. 6) and an imaging system for counting the medications on the counting tray 318. The barcode scanner 102 is used to scan a barcode on a label of a bulk container retrieved from the device 54 or other location within the pharmacy and may be implemented similar to the barcode scanner 78. The contents of the bulk container may then be placed on the counting tray 318 for counting by the pre-counter 314. The counting tray 318 may be replaceable for cleaning and to inhibit cross-contamination between different types of medications. The counting tray 318 is pivotably attached to a housing of the pre-counter 314 such that a user can lift the counting tray 318 to direct the medications on the counting tray 318 into the funnel 330 without having to touch the medications. The funnel 330 is shaped to guide the medications from the counting tray 318 into the cartridge slot 334. The cartridge slot 334 is provided below the funnel 330 to receive a cartridge 158. In some embodiments, the pre-counter 314 may include a mechanism to rotate the wheel 860 or otherwise agitate the cartridge 158 to help make room for the pills to be funneled into the cartridge 158.

The counting tray 318 may be transparent or translucent such that a lighting system 126 (see FIG. 6) underneath the counting tray 318 can illuminate the contents of the counting tray 318. Once illuminated, the camera system 322 may capture an image of the contents of the counting tray 318 to commence counting. The display 326 may be used to display the scanned barcode information and to display the count of the medications placed on the counting tray 318. Based on the displayed information, a pharmacist or technician may add or remove medications from the counting tray 318 until the correct amount of medications is placed on the counting tray 318. When the correct amount of medications is placed on the counting tray 318, the user may transfer the contents of the counting tray 318 to the cartridge 158 (FIG. 7) of the automatic packager 38 placed in the cartridge slot 334. The user may transfer the contents of the counting tray 318 by lifting the counting tray 318 to guide the medications into the cartridge 158 through the funnel 330. In some embodiments, a lockout mechanism may be provided for the counting tray 318. The lockout mechanism of the counting tray 318 prevents the counting tray 318 from being lifted when an incorrect amount of medications are placed on the counting tray 318. The lockout mechanism of the counting tray 318 may be unlocked when the correct amount of medications are placed on the counting tray 318, such that the pharmacist may lift the counting tray 318 to transfer the medications to the cartridge 158.

Figure 14:
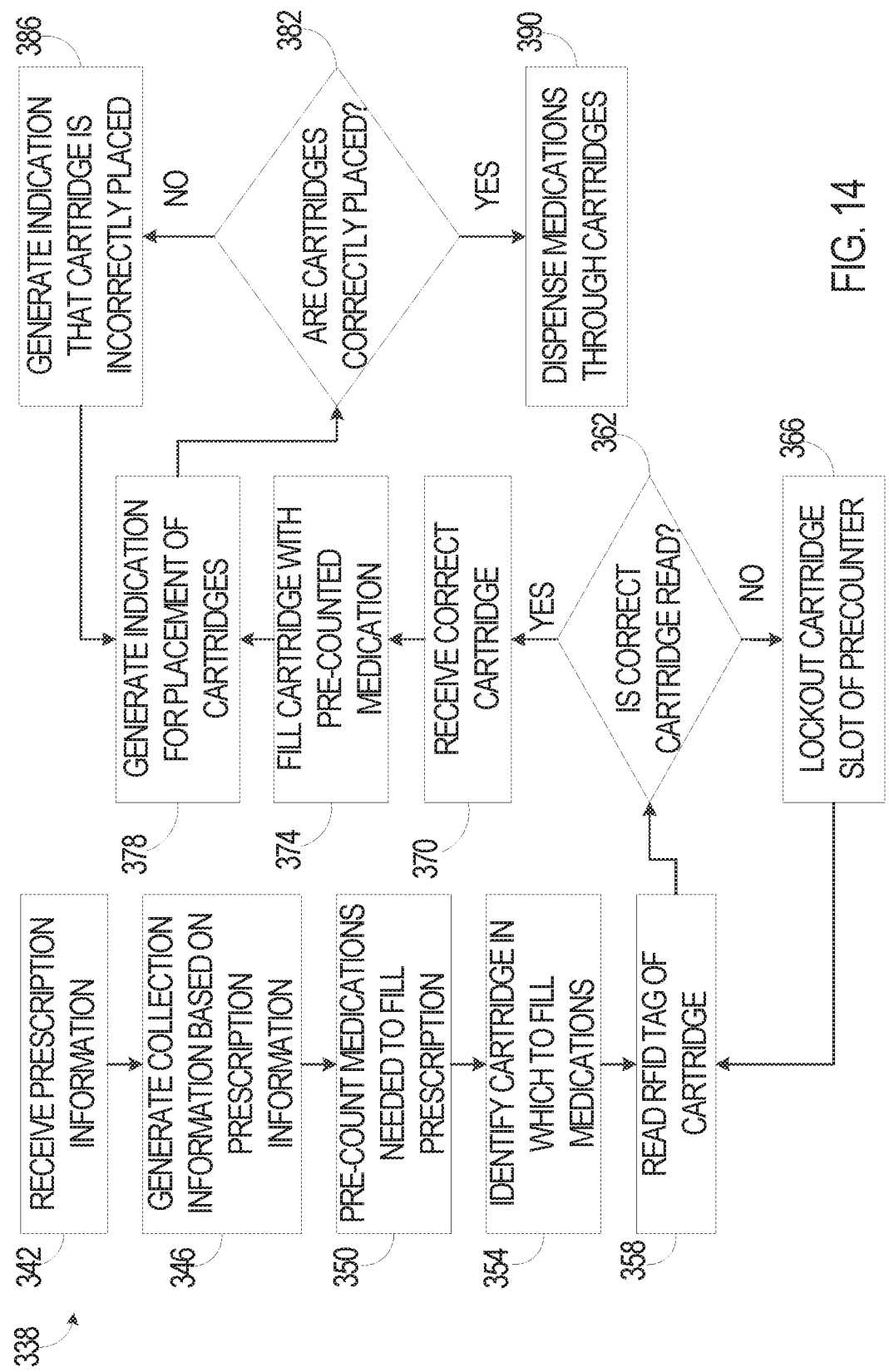
FIG. 14 is a flowchart of a method of filling cartridges in accordance with some embodiments.

FIG. 14 is a flowchart illustrating one example method 338 of filling cartridges 158. Although the method 338 includes specific blocks, all the blocks need not be performed or performed in the order presented. As illustrated in FIG. 14, the method 338 includes receiving, using the electronic processor 14, prescription information (at block 342). Typically, a pharmacist examines a prescription presented by a patient to fill the prescription. The pharmacist may scan or manually enter the prescription information including dosage, quantity, and drug information through an input/output interface 26 of the pharmacy management system 10. For example, the input/output interface 26 may include a scanner and/or a separate computer console to enter prescription information.

The method 338 also includes generating, using the electronic processor 14, collection information based on the prescription information (at block 346). The electronic processor 14 receives the prescription information and generates collection information for a pharmacist to collect bulk containers including the medications listed on the prescription. The electronic processor 14 may use a look-up table to determine the location (for example, an aisle and/or bin number) of a medication listed on the prescription. The electronic processor 14 may then print or display the collection information listing the medications in the prescription and the location of the bulk containers including the medications. Additionally, in some embodiments, the collection information may also include an identification number of a cartridge 158 for each of the medications listed in the prescription. The pharmacist collects the bulk containers based on the collection information provided on, for example, a printed collection sheet.

The method 338 further includes pre-counting, using the pre-counter 314, the medications needed to fill the prescription (at block 350). A method for pre-counting the medications is described above with respect to FIG. 11. The method 338 further includes identifying a cartridge 158 in which to fill the medications (at block 354). Either the pre-counter 314 or the electronic processor 14 may identify the cartridge 158 for filling. For example, as described above, the electronic processor 14 may identify the cartridge 158 on the collection sheet. The electronic processor 14 then transmits the identification information (e.g., an identification number) of the cartridge(s) 158 to the pre-counter 314. The pre-counter 314 may identify the cartridge 158 based on the scanned bulk container. For example, when a bulk cartridge is scanned at the pre-counter 314, the pre-counter 314 identifies a cartridge 158 compatible with the medication in the bulk container. Different cartridges 158 may be used to dispense medications of different sizes. Additionally, some cartridges 158 may be reserved for allergenic medications (e.g., penicillin) to reduce cross-contamination. The pre-counter 314 identifies the cartridge 158 compatible with the medications in the bulk container and displays identification information (e.g., a cartridge number) on the display 326 of the pre-counter 314.

The method 338 includes reading, using the pre-counter 314, an RFID tag of the cartridge 158 to receive identification information of the cartridge 158 (at block 358). Once the appropriate cartridge 158 is identified at block 354, the pharmacist may grab the identified cartridge 158 and scan the RFID tag of the cartridge 158 at the pre-counter 314. The method 338 further includes determining, using the pre-counter 314, whether the correct cartridge 158 is read (at block 362). The pre-counter 314 compares the received identification information received from the RFID tag scan to the identification information of the correct cartridge 158 (e.g., the cartridge 158 identified by the electronic processor 14 or the pre-counter 314 at block 354) to determine whether the pharmacist grabbed the correct cartridge 158.

In response to determining that an incorrect cartridge 158 is read at block 358, the method 338 includes locking out the cartridge slot 334 of the pre-counter 314 (at block 366). The pre-counter 314 includes doors that may be locked out by a solenoid. When locked-out, the pharmacist cannot insert the cartridge 158 into the cartridge slot 162. The pre-counter 314 locks out the cartridge slot 334 until the correct cartridge 158 is scanned at the pre-counter 314.

In response to determining that the correct cartridge 158 is read at block 358, the method 338 includes receiving, at the cartridge slot 334 of the pre-counter 314, the correct cartridge 158 (at block 370). The method 338 then includes filling, using the pre-counter 314, the cartridge 158 with the pre-counted medications (at block 374). In some embodiments, the chain of custody information is updated to include which cartridge 334 is positioned in the slot (e.g., via the RFID tag on the cartridge 334). Additionally, the type of the medications loaded into the cartridge and/or the number of medications loaded into the cartridge are also updated into the chain of custody information.

The method 338 further includes generating, using the automatic packager 38, an indication for placement of filled cartridges 158 (at block 378). The automatic packager 38 may generate an indication using an indicator system of the automatic packager 38. For example, when the prescription includes three different medications to be packaged, the automatic packager 38 may activate a blue LED of three cartridge slots 162 (also referred to as a cartridge mechanism) to indicate that the filled cartridges 158 should be placed in the activated cartridge slots 162. The automatic packager 38 may activate the indicator system (e.g., an LED) of a first cartridge slot 162 to guide the pharmacist to place a first cartridge 158 at the first cartridge slot 162. The automatic packager 38 may then activate the indicator system of a second cartridge slot 162 to guide the pharmacist to place the second cartridge 158 at the second cartridge slot 162 and so on.

The method 338 also includes determining, using the automatic packager 38, whether the cartridges 158 are correctly placed on the automatic packager 38 (at block 382). The automatic packager 38 may read the RFID tag of the cartridge 158 using an RFID antenna at the cartridge slot 162 to determine whether the correct cartridge 158 is placed in the cartridge slot 162. When a cartridge 158 is incorrectly placed on the cartridge slot 162, the method 338 includes generating an indication that the cartridge 158 is incorrectly placed (at block 386). For example, as described above, the automatic packager 38 may activate the red LED of the indicator system 990 of the corresponding cartridge mechanism 845. In some embodiments, the cartridge slot 162 may include a lockout mechanism (e.g., a solenoid lockout mechanism on a cartridge mechanism of the cartridge slot 162) that prevents an incorrect cartridge 158 from being loaded into the cartridge slot 162. The automatic packager 38 may lockout the cartridge slot 162 until the correct cartridge 158 is placed in the cartridge slot 162. In some embodiments, the lockout mechanism of the cartridge slot 162 may also prevent the cartridge 158 from being removed until the dispensing process is complete.

When the cartridges 158 are correctly placed on the automatic packager 38, the method 338 includes dispensing, using the automatic packager 38, the medications through the cartridges 158 (at block 390). In some embodiments, once the dispensing process is complete, the automatic packager 38 may indicate which cartridges 158 are ready to be removed. For example, as described above, the automatic packager 38 may activate the LEDs (e.g., a green LED) to indicate that the cartridges 158 are ready to be removed.

Figure 15:
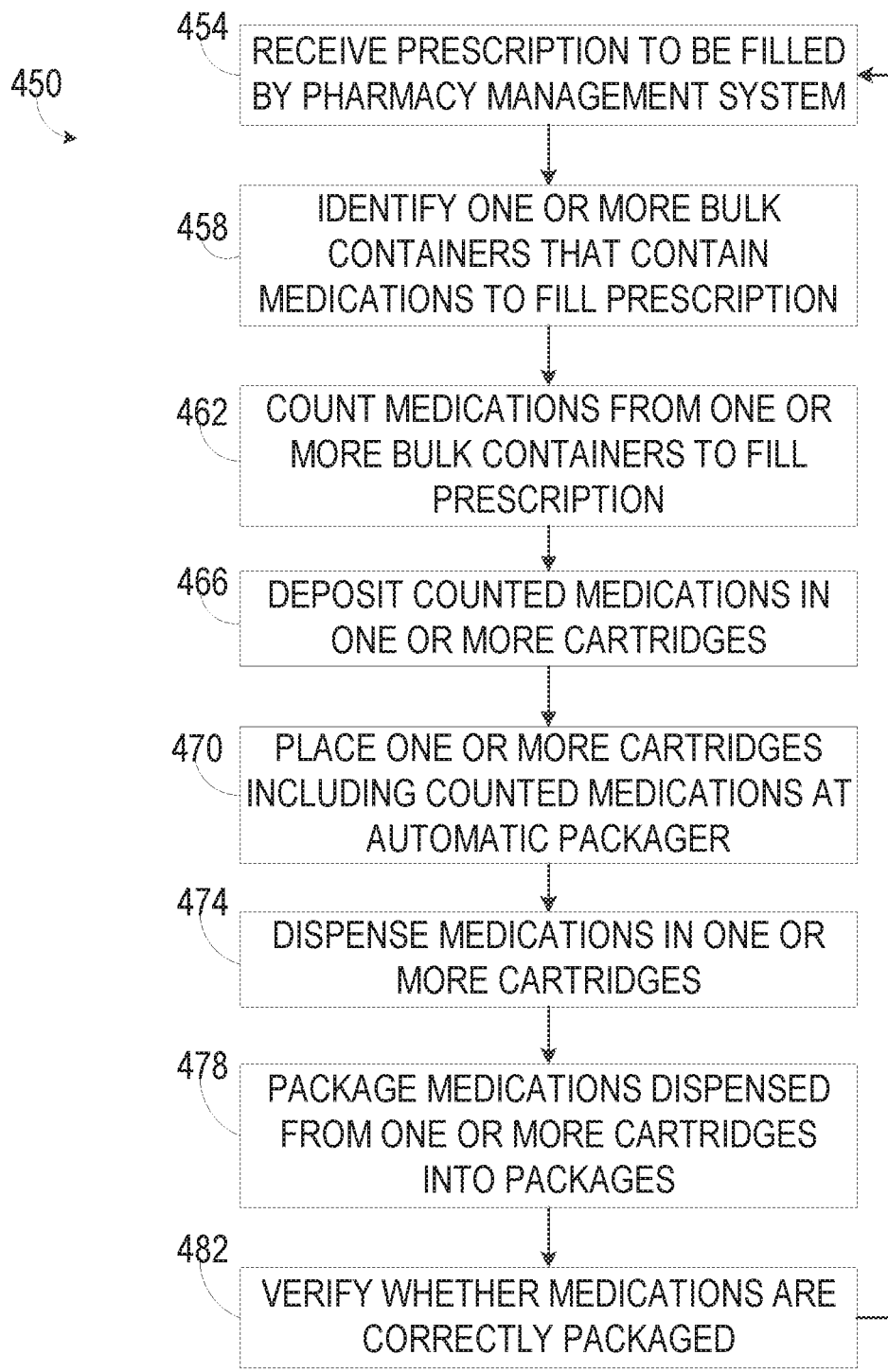
FIG. 15 is a flowchart of a method of filling a prescription in accordance with some embodiments.

FIG. 15 is a flowchart illustrating one example method 450 of filling a prescription in a pharmacy. Although the method 450 includes specific blocks, all the blocks need not be performed or performed in the order presented. As illustrated in FIG. 15, the method 450 includes receiving, at the electronic processor 14 of the pharmacy management system 10, a prescription to be filled by the pharmacy management system 10 (at block 454). As discussed above, a pharmacist examines a prescription presented by a patient to fill the prescription. The pharmacist may scan or manually enter the prescription information including dosage, quantity, and drug information through the input/output interface 26 of the pharmacy management system 10. In some embodiments, the method 450 also includes generating, using the electronic processor 14, an information sheet for filling the prescription. The information sheet lists the medications needed to fill the prescription.

The method 450 also includes identifying, at the pre-counter 314, one or more bulk containers that contain medications to fill the prescription (at block 458). In some embodiments, the method 450 includes retrieving the one or more bulk storage containers containing the medications needed to fill the prescription. The pre-counter 314 associates the one or more cartridges 158 with one or more medications listed on the prescription. In some embodiments, identifying the one or more bulk containers that contain medications to fill the prescription includes scanning, using the pre-counter 314, the one or more bulk containers identified at the pre-counter 314.

The method 450 also includes counting, using the pre-counter 314, medications from the one or more bulk containers to fill the prescription (at block 462). The pre-counter 314 prompts to add or remove medications from the pre-counter 314. An example method of counting medications using the pre-counter 314 is described above with respect to FIG. 11. The method 450 also includes depositing the counted medications in one or more cartridges 158 (at block 466). Once the required number of medications is placed on the counting tray 318 of the pre-counter 314, the pharmacist fills a cartridge 158, for example, by emptying the counting tray 318 into the cartridge 158 using the funnel 118 and the funnel gate 122. In some embodiments, the method 450 also includes determining an expected medication type to be counted using the pre-counter. When the medications on the pre-counter do not match the expected medication type, the pre-counter 314 prompts the user to remove medications from the pre-counter.

The method 450 also include placing the one or more cartridges 158 including the counted medications at the automatic packager 38 (at block 470). The filled cartridges 158 are placed in cartridge slots 162 of the automatic packager 38 to begin packaging the medications. As discussed above, the automatic packager 38 may generate an indication using an indicator system of the automatic packager 38. For example, when the prescription includes three different medications to be packaged, the automatic packager 38 may activate a blue LED of three cartridge slots 162 (also referred to as a cartridge mechanism) to indicate that the filled cartridges 158 should be placed in the activated cartridge slots 162. The automatic packager 38 may activate the indicator system (e.g., an LED) of a first cartridge slot 162 to guide the pharmacist to place a first cartridge 158 at the first cartridge slot 162. The automatic packager 38 may then activate the indicator system of a second cartridge slot 162 to guide the pharmacist to place the second cartridge 158 at the second cartridge slot 162 and so on.

The method 450 also includes dispensing, using the automatic packager 38, the medications in the one or more cartridges 158 (at block 474). Dispensing the medications includes singulating the medications in the one or more cartridges 158 for individually dispensing the medications. For example, a controller of the universal feed cassette 150, or the packager electronic processor 202 controls each loaded cartridge 158 to individually dispense medications to the packaging unit 154. The control signals are provided to the motor assembly to operate the motor 950. As discussed above, when the motor 950 is driven, the shaft 955 rotates the wheel 860 to the individually dispense the medications 180. The automatic packager 38 then verifies each medication as the medication is dispensed from the one or more cartridges 158.

The method 450 also includes packaging, using the packaging unit 154 of the automatic packager 38, medications dispensed from the one or more cartridges 158 into packages (at block 478). As described above, the medications may be packaged into pouches or strip packages to be provided to a customer.

The method 450 also includes verifying, using the automatic packager 38, whether the medications are correctly packaged (at block 482). In some embodiments, the method 450 includes capturing, at the pre-counter 314, an image of the medications for verification. The pre-counter 314 determines one or more characteristics of the medications listed on the prescription and transmits the one or more characteristics of the medications to the automatic packager 38. The automatic packager 38 verifies that the correct medications are packaged by the packaging unit 154 based on the one or more characteristics of the medications received from the pre-counter 314. In some embodiments, the automatic packager 38 captures a first image of the medications during singulation of the medications for a first verification. The automatic packager 38 also captures a second image of the medications during packaging of the medications dispensed from the one or more cartridges 158 into packages. Verifying whether the medications are correctly packaged may be based on the second image.

Various features and advantages of the invention are set forth in the following claims.

The invention claimed is:

1. A method for filling a prescription in a pharmacy, the method comprising:
   receiving, at an electronic processor of a pharmacy management system, a prescription to be filled by the pharmacy management system;
   identifying, at a pre-counter, a plurality of bulk containers that contain types of medications listed on the prescription;
   counting, using the pre-counter, medications from the plurality of bulk containers;
   depositing the counted medications in a plurality of cartridges such that each type of medications is deposited in a separate one of the plurality of cartridges;
   placing the plurality of cartridges including the counted medications at the automatic packager;
   dispensing, using the automatic packager, the medications from the plurality of cartridges;
   packaging, using a packaging unit of the automatic packager, medications dispensed from the plurality of cartridges into packages; and
   verifying, using the automatic packager, whether the medications are correctly packaged in the packages.

2. The method of claim 1, further comprising generating, using the electronic processor, an information sheet for filling the prescription, the information sheet listing the types of medications needed to fill the prescription.

3. The method of claim 1, further comprising:
   capturing, at the pre-counter, an image of a type of medication from the plurality of types of medication for verification;
   determining, using the pre-counter, one or more characteristics of the type of medication based on image processing of the image; and
   transmitting, using the pre-counter, the one or more characteristics of the type of medication to the automatic packager, wherein the automatic packager verifies correct medications are packaged by the packaging unit based on the one or more characteristics of the type of medication received from the pre-counter.

4. The method of claim 1, further comprising:
   singulating, using the automatic packager, the medications in the plurality of cartridges such that each medication in a plurality of medications in a cartridge of the plurality of cartridges is individually dispensed from the cartridge to a packaging unit of the automatic packager;
   capturing a first image of the medications during singulation of the medications;
   verifying, using the automatic packager, that a type of medication detected based on image processing of the first image matches a type of medication of the plurality of medications; and
   capturing a second image of the medications during packaging of the medications dispensed from the plurality of cartridges into packages, wherein verifying whether the medications are correctly packaged is based on the second image.

5. The method of claim 1, further comprising associating the plurality of cartridges with the types of medications listed on the prescription such that each cartridge of the plurality of cartridges is assigned to one type of the types of medications.

6. The method of claim 1, further comprising scanning, using the pre-counter, the plurality of bulk containers identified at the pre-counter.

7. The method of claim 1, further comprising:
   determining, using the pre-counter whether a count of the medications on the pre-counter matches a number of the medications listed on the prescription; and
   prompting, using the pre-counter, to add or remove medications from the pre-counter when the count of the medications does not match the number of the medications.

8. The method of claim 1, further comprising:
   determining an expected type of medication to be counted using the pre-counter; and
   prompting, using the pre-counter, to remove medications from the pre-counter when a type of medication on the pre-counter does not match the expected type of medication.

9. The method of claim 1, wherein the automatic packager is a strip packager.

10. A method for filling a prescription in a pharmacy, the method comprising:
    receiving, at an electronic processor of a pharmacy management system, a prescription to be filled by the pharmacy management system;
    identifying, at a pre-counter, a bulk container that contains a type of medication listed on the prescription;
    counting, using the pre-counter, medications from the bulk container when the medications are deposited on a counting tray of the pre-counter;
    determining, using the pre-counter, whether a number of the medications on the counting tray matches a number listed on the prescription for the type of medication;
    prompting, using the pre-counter, to add or remove pills from the counting tray when the number of medications does not match the number listed on the prescription for the type of medication;
    depositing the counted medications in a cartridge;
    moving cartridge including the counted medications from the pre-counter to an automatic packager;
    verifying, using the automatic packager, each medication as the medication is dispensed from the cartridge; and
    packaging, using a packaging unit of the automatic packager, medications dispensed from the cartridge into packages.

11. The method of claim 10, further comprising verifying, using the automatic packager, whether the medications are correctly packaged.

12. The method of claim 11, further comprising:
    capturing, at the pre-counter, an image of the medications for verification;

determining, using the pre-counter, one or more characteristics of the medications listed on the prescription based on image processing of the image; and transmitting, using the pre-counter, the one or more characteristics of the medications to the automatic packager, wherein the automatic packager verifies correct medications are packaged by the packaging unit based on the one or more characteristics of the medications received from the pre-counter.

13. The method of claim 10, further comprising associating, using the pre-counter, the cartridge with the type of medication.

14. The method of claim 13, wherein the cartridge is a first cartridge, the method further comprising:
displaying identification information of the first cartridge on a display of the pre-counter;
scanning a second cartridge not associated with type of medication when the identification information of the first cartridge is displayed; and
inhibiting transfer of medications from the pre-counter to the second cartridge in response to scanning the second cartridge.

15. The method of claim 10, wherein the automatic packager is a separate device from the pre-counter such that the medications are manually transferred between the pre-counter and the automatic packager.

16. A method for filling a prescription in a pharmacy, the method comprising:
receiving, at an electronic processor of a pharmacy management system, a prescription to be filled by the pharmacy management system;
identifying, at a pre-counter, a bulk container that contains a type of medication listed on the prescription;
counting, using the pre-counter, medications from the bulk container;
packaging, using a packaging unit of an automatic packager, medications counted at the pre-counter, the automatic packager being a separate device from the pre-counter such that the medications are manually transferred between the pre-counter and the automatic packager;
capturing one or more images of the medications counted at the pre-counter; and
verifying, using the automatic packager, whether the medications are correctly packaged based on the one or more images of the medications.

17. The method of claim 16, wherein counting medications includes prompting a user to add or remove medications from the pre-counter.

18. The method of claim 16, further comprising:
capturing, at the pre-counter, an image of the medications for verification;
determining, using the pre-counter, one or more characteristics of the medications listed on the prescription based on image processing of the image; and
transmitting, using the pre-counter, the one or more characteristics of the medications to the automatic packager, wherein the automatic packager verifies correct medications are packaged by the packaging unit based on the one or more characteristics of the medications received from the pre-counter.

19. The method of claim 16, further comprising:
determining, using the pre-counter, whether a count of the medications from the bulk container matches a number listed on the prescription for the type of medications;
prompting, using the pre-counter, to add or remove pills from the pre-counter when the count does not match the number listed on the prescription for the type of medication.

20. The method of claim 16, wherein the medications are deposited on a counting tray of the pre-counter for counting and image capture by the pre-counter.

21. A method for filling a prescription in a pharmacy, the method comprising:
receiving, at an electronic processor of a pharmacy management system, a prescription to be filled by the pharmacy management system;
placing a cartridge including a type of medication listed on the prescription at an automatic packager;
singulating, using the automatic packager, the medications in the cartridge such that each medication of the medications is individually dispensed from the cartridge to a packaging unit of the automatic packager;
verifying, using the automatic packager, each medication as the medication is dispensed from the cartridge;
capturing an image of the each medication as the medication is being dispensed from the cartridge;
packaging, using a packaging unit of the automatic packager, medications dispensed from the cartridge into packages; and
verifying, using the automatic packager, whether the medications are correctly packaged.

22. The method of claim 21, further comprising:
capturing a first image of each medication during singulation of the medications;
verifying whether each singulated medication matches the type of medication based on image processing of the first image; and
capturing a second image of the medications during packaging of the medications dispensed from the cartridge into packages, wherein verifying whether the medications are correctly packaged is based on the second image.

23. The method of claim 21, wherein the cartridge is a first cartridge and the type of medication is a first type of medication, the method further comprising:
placing a second cartridge including a second type of medication listed on the prescription at the automatic packager, wherein a first medication from the first cartridge and a second medication from the second cartridge are packaged in a single package.

24. A method for filling a prescription in a pharmacy, the method comprising:
receiving, at an electronic processor of a pharmacy management system, a prescription to be filled by the pharmacy management system;
identifying, at a pre-counter, a bulk container that contains a type of medication listed on the prescription;
capturing, at the pre-counter, images of medications from the bulk container deposited on the pre-counter;
counting, using the pre-counter, the medications based on the images of the medications;
determining, using the pre-counter, one or more characteristics of the medications based on image processing of the images of the medications; and
transmitting, using the pre-counter, the one or more characteristics of the medications to an automatic packager, wherein the automatic packager verifies correct medications are packaged by a packaging unit based on the one or more characteristics of the medications received from the pre-counter.

25. The method of claim 24, wherein counting medications includes prompting a user to add or remove medications from the pre-counter.

26. The method of claim 24, further comprising verifying whether the medications match the type of medication based on the one or more characteristics of the medications.

27. The method of claim 26, wherein the automatic packager is a separate device from the pre-counter such that the medications are manually transferred between the pre-counter and the automatic packager.

* * * * *